(12) United States Patent
Barten et al.

(10) Patent No.: US 12,241,074 B2
(45) Date of Patent: Mar. 4, 2025

(54) GENOME EDITING-BASED CROP ENGINEERING AND PRODUCTION OF BRACHYTIC PLANTS

(71) Applicant: Monsanto Technology LLC, St. Louis, MO (US)

(72) Inventors: Ty J. Barten, Ankeny, IA (US); Edward J. Cargill, Chesterfield, MO (US); Jonathan C. Lamb, Wildwood, MO (US); Bryce Lemke, Nevada, IA (US); Linda A. Rymarquis, High Ridge, MO (US); Dennis H. Yang, Ballwin, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/472,140

(22) PCT Filed: Dec. 21, 2017

(86) PCT No.: PCT/US2017/067888
§ 371 (c)(1),
(2) Date: Jun. 20, 2019

(87) PCT Pub. No.: WO2018/119225
PCT Pub. Date: Jun. 28, 2018

(65) Prior Publication Data
US 2020/0140874 A1    May 7, 2020

Related U.S. Application Data

(60) Provisional application No. 62/438,370, filed on Dec. 22, 2016.

(51) Int. Cl.
| C12N 15/82 | (2006.01) |
| A01H 1/06 | (2006.01) |
| A01H 5/10 | (2018.01) |
| A01H 6/46 | (2018.01) |
| C07K 14/415 | (2006.01) |

(52) U.S. Cl.
CPC .......... *C12N 15/8262* (2013.01); *A01H 1/06* (2013.01); *A01H 5/10* (2013.01); *A01H 6/4684* (2018.05); *C07K 14/415* (2013.01); *C12N 15/8213* (2013.01); *C12N 15/8261* (2013.01)

(58) Field of Classification Search
None
See application file for complete search history.

(56) References Cited

U.S. PATENT DOCUMENTS

| 5,159,135 A | 10/1992 | Umbeck |
| 5,188,958 A | 2/1993 | Moloney et al. |
| 5,463,174 A | 10/1995 | Moloney et al. |
| 5,538,880 A | 7/1996 | Lundquist et al. |
| 5,550,318 A | 8/1996 | Adams et al. |
| 5,591,616 A | 1/1997 | Hiei et al. |
| 5,750,871 A | 5/1998 | Moloney et al. |
| 5,824,877 A | 10/1998 | Hinchee et al. |
| 6,153,812 A | 11/2000 | Fry et al. |
| 6,160,208 A | 12/2000 | Lundquist et al. |
| 6,194,636 B1 | 2/2001 | McElroy et al. |
| 6,232,526 B1 | 5/2001 | McElroy et al. |
| 6,384,301 B1 | 5/2002 | Martinell et al. |
| 6,399,861 B1 | 6/2002 | Anderson et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 2002/0162142 A1 | 10/2002 | Johal et al. |
| 2004/0216189 A1 | 10/2004 | Houmard et al. |
| 2006/0141495 A1 | 6/2006 | Wu |
| 2009/0070898 A1 | 3/2009 | Allen et al. |
| 2011/0035839 A1 | 2/2011 | Lutfiyya et al. |
| 2011/0296555 A1 | 12/2011 | Ivashuta et al. |
| 2014/0068797 A1 | 3/2014 | Doudna et al. |
| 2014/0273235 A1 | 9/2014 | Voytas et al. |
| 2015/0067922 A1 | 3/2015 | Yang et al. |

(Continued)

FOREIGN PATENT DOCUMENTS

| CN | 102 373 278 A | 3/2012 |
| WO | WO 01/34818 A2 | 5/2001 |
| WO | WO 01/34819 A2 | 5/2001 |

OTHER PUBLICATIONS

Fonfara et al. Phylogeny of Cas9 determines functional exchangeability of dual-RNA and Cas9 among orthologous type II CRISPR-Cas systems. Nucleic Acid Res. Feb. 2014;42(4):2577-90. Epub Nov. 22, 2013 (Year: 2014).*

(Continued)

*Primary Examiner* — Cynthia E Collins
(74) *Attorney, Agent, or Firm* — MORRISON & FOERSTER LLP

(57) ABSTRACT

Disclosed herein are plants exhibiting a semi-dwarf phenotype with reduced plant height compared to control wildtype plants. Some of the disclosed semi-dwarf plants comprise at least one non-natural brachytic mutation in which the activity of a BR2 gene is reduced. Also disclosed are methods for producing a semi-dwarf corn plant using a CRISPR based genome editing system.

14 Claims, 7 Drawing Sheets

Specification includes a Sequence Listing.

(56) References Cited

U.S. PATENT DOCUMENTS

2016/0208272 A1 7/2016 Cigan et al.
2016/0319375 A1* 11/2016 Barten .................... A01H 1/04

OTHER PUBLICATIONS

Multani et al. Loss of an MDR transporter in compact stalks of maize br2 and sorghum dw3 mutants. Science. Oct. 3, 2003;302(5642):81-4. (Year: 2003).*
Endo et al. Efficient targeted mutagenesis of rice and tobacco genomes using Cpf1 from Francisella novicida. Sci. Rep. Dec. 1, 2016;6:38169. (Year: 2016).*
Xing et al. A rare SNP mutation in Brachytic2 moderately reduces plant height and increases yield potential in maize. J. Exp. Bot. Jul. 2015;66(13):3791-802. Epub Apr. 28, 2015. (Year: 2015).*
Zhu et al. Efficiency and Inheritance of Targeted Mutagenesis in Maize Using CRISPR-Cas9. J. Gent. Genomics. Jan. 20, 2016;43(1):25-36. Epub Dec. 21, 2015. (Year: 2016).*
Cassani et al. The brachytic 2 and 3 maize double mutant shows alterations in plant growth and embryo development. Plant Growth Regul. (2011) 64:185-192. (Year: 2011).*
Pilu et al. Isolation and characterization of a new mutant allele of brachytic 2 maize gene. Molecular Breeding 20, 83-91 (2007). (Year: 2007).*
Shah et al. Protospacer recognition motifs: mixed identities and functional diversity. RNA Biol. May 2013;10(5):891-9. Epub Feb. 12, 2013. (Year: 2013).*
Extended European Search Report dated May 19, 2020, in European Patent Application No. 17885381.8.
Beurdelet et al., "Compact designer TALENs for efficient genome engineering," *Nature Communications*, 4:1762 (2013).
Cassani et al., "The brachytic 2 and 3 maize double mutant shows alterations in plant growth and embryo development," *Plant Growth Regul.*, 64:185-192(2011).
Cermak et al., "Efficient design and assembly of custom TALEN and other TAL effector-based constructs for DNA targeting," *Nucleic Acids Research*, 39:e82 (2011).

Chenna et al., "Multiple sequence alignment with the Clustal series of programs," *Nulceic Acids Research*, 31:3497-3500 (2003).
Cong et al., "Multiplex genome engineering using CRISPR/Cas systems," *Science*, 339:819-823 (2013).
Doyle et al., "TAL Effector-Nucleotide Targeter (TALE-NT) 2.0: tools for TAL effector deisgn and target prediction," *Nucleic Acids Research*, 40:W117-122 (2012).
Gabsalilow et al., "Site- and strand-specific nicking of DNA by fusion proteins derived from MutH and I-SceI of TALE repeats," *Nucleic Acids Research*. 41:e83 (2013).
International Search Report and Written Opinion mailed in May 4, 2018 in PCT/2017/067888.
Kempton, "Heritable characters of maize III. Brachytic culms," *Jour. Heredity* 11:111-115 (1920).
Larkin et al., "Clustal W and Clustal X version 2.0," *Bioinformatics*, 23: 2947-48 (2007).
Makarova et al.,"An updated evolutionary classification of CRISPR-Cas systems," *Nature Reviews Microbiology*, (2015) doi: 10.1038/nrmicro3569.
Multani et al., Loss of an MDR transporter in compact stalks of maize br2 and sorghum dw3 mutants, *Science*, 302(5642)81-84 (2003).
Pilu et al., "Isolation and characterization of a new mutant allele of brachytic 2 maize gene," *Molecular Breeding*, 20:83-91 (2007).
Thompson et al., "Clustal W: Improving the sensitivity of progressive multiple sequence alignment through sequence weighting, position-specific gap penalties and weight matrix choice," *Nucleic Acids Research*22: 4673-4680 (1994).
Xing et al., "A rare SNP mutation in Brachytic2 moderately reduces plant height and increases yield potential in maize," *J. Exp. Bot.*, 66: 3791-802 (2015).
Yanik et al., "TALE-PvuII Fusion Proteins—Novel Tools for Gene Targeting," *PLoS One*, 8(12):e82539 (2013). doi: 10.1371/journal.pone.0082539. eCollection 2013.
Zetsche et al., "Cpf1 is a single RNA-guided endonuclease of a class 2 CRISPR-Cas system," *Cell*, (2015) doi: 10.1016/j.cell.2015.09.038.
GenBank Accession No. AY366085.1, last updated Oct. 21, 2003, located at <https://www.ncbi.nlm.nih.gov/nuccore/AY366085.1/>, last visited on Sep. 12, 2020, three pages.

* cited by examiner

GENOME EDITING-BASED CROP ENGINEERING AND PRODUCTION OF BRACHYTIC PLANTS

CROSS-REFERENCE TO RELATED APPLICATION AND INCORPORATION OF SEQUENCE LISTING

This application is a U.S. National Stage Application of International Application No. PCT/US2017/067888 filed Dec. 21, 2017, which claims benefit under 35 U.S.C. § 119 (e) of U.S. Provisional Appln. No. 62/438,370, filed Dec. 22, 2016, herein incorporated by reference in their entireties. The sequence listing that is contained in the filed named "P34495US01.txt." which is 32,113 bytes (measured in operating system MS-Windows) and was created on Jun. 19, 2019, is filed herewith and incorporated herein by reference.

BACKGROUND

Field

The present disclosure relates to compositions and methods for producing a modified plant exhibiting semi-dwarf phenotype.

Related Art

A sustained increase in crop yield, e.g., in wheat and rice has been achieved in the past few decades. This increase is partly attributed to the use of fertilizers and pesticides as well as the introduction of semi-dominant dwarfing mutations which reduce plant height. Taller plants are more likely to lodge in response to heavy rainfall or wind, and the heavier inflorescences of high-yield elite breeds also make them more susceptible to lodging. In contrast, crops with a shorter stature are more resistant to lodging. Moreover, dwarf and semi-dwarf traits can also allow higher planting densities and help improve crop harvest index and nitrogen response. The introduction of dwarf varieties of wheat and rice served as a cornerstone of the so-called "Green revolution" of the late 20th century.

Maize (Zea mays L.), a member of the Gramineae genus, provides cylindrical stalks similar to those from other grasses. The maize stalks are thick and spongy inside and divided into parts called internodes and nodes. The number of nodes ranges from between 8 to 40 depending on the variety and growing conditions. Commercial hybrid maize normally grows to a height of typically more than 2 meters with each plant having either one or two ears. The ear normally grows about one-third of the way up the plant or about three feet from the ground. Consequently a maize plant, while providing a large ear in addition to a substantial leaf and stalk structure, can have a considerable mechanical stability problem. Reducing the height of a maize plant can improve the mechanical stability of the plant.

More than 40 monogenic dwarfing mutants have been described in maize. A majority of these mutants lead to great reductions in grain yield and, consequently, they have not been used to enhance crop yield in germplasm that is sensitive to lodging. Therefore, an important but difficult goal in corn breeding is to identify and use dwarf or semi-dwarf mutations which confer a short stature without severely impacting other organs, especially reproductive organs (e.g., ears).

In maize, brachytic mutants show a short stature due to a shortening of the internode length without a corresponding reduction in the number of internodes or the number and size of other organs, including the leaves, ear and tassel. See Kempton J. Hered., 11:111-115(1920); Pilu et al., Molecular Breeding, 20:83-91(2007). BR genes are plant hormones that regulate a number of major plant growth and developmental processes. Three brachytic br mutants have been isolated in maize to date: brachytic1 (br1), brachytic2 (br2) and brachytic3 (br3). Both br1 and br3 mutations cause a reduction in corn plant height which has been thought too severe for commercial exploitation due to potential impacts over yield. In contrast, the br2 mutant has particular agronomic potential because of the shortening of the internodes of the lower stalk with no obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with Gibberellins, auxins, brassinosteroids and cytokinins, suggesting that the biosynthesis of these hormones is not modified by the br2 mutation.

Multani et al. identified a genomic sequence of the Br2 gene and deposited it under GenBank Accession No. AY366085. See Science, 302(5642)81-84 (2003). Br2 was annotated to encode a putative protein similar to adenosine triphosphate (ATP)-binding cassette transporters of the multidrug resistant (MDR) class of P-glycoproteins (PGPs). The predicted BR2 protein consists of two similar halves, each containing six putative transmembrane domains and an intracellular ATP nucleotide-binding domain. The length of the br2 gene is 7139 bp with a coding sequence of 4185 bp. Pilu et al. reported a br2-23 allele having an 8-bp deletion in the 3' end of the Br2 gene and claimed a direct relationship between this deletion and the brachytic phenotype in their br2-23 plants. See Pilu et al., Molecular Breeding, 20:83-91(2007). Nevertheless, the use of brachytic mutations in corn has not been exploited commercially partly because of the severity of the available brachytic mutant alleles.

There is a need in corn research to engineer corn plants that provides novel and commercially relevant brachytic mutant alleles, e.g., those conferring a semi-dwarf phenotype and maintaining or improving kernel yield.

SUMMARY

Figure 1:
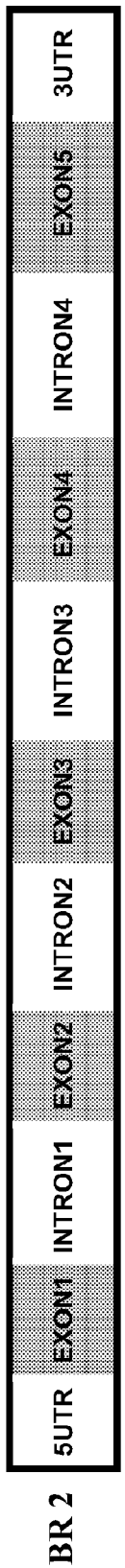
FIG. 1 schematically illustrates the structure of the BR2 gene.

The present specification provides a corn plant comprising at least one non-natural brachytic mutation, where the corn plant exhibits a semi-dwarf phenotype compared to a control corn plant not comprising the at least one non-natural brachytic mutation when grown under comparable conditions.

The present specification also provides a brachytic corn plant comprising at least one non-natural brachytic mutation.

Also provided by the present specification is a brachytic corn plant comprising at least one non-natural brachytic mutant allele.

Further provided by the present specification is a corn plant comprising at least one non-natural brachytic mutation exhibiting a semi-dwarf phenotype.

In one aspect, the present specification provides a corn plant comprising at least one non-natural brachytic mutant allele exhibiting a semi-dwarf phenotype.

In another aspect, the present specification provides a modified corn plant comprising a non-naturally occurring mutation in a BR gene reducing the activity of the BR gene, where the mutation is not introduced via transposon.

In yet another aspect, the present specification provides a modified corn plant comprising a modified BR2 gene with reduced activity, where the modified corn plant does not comprise a br2-23 brachytic allele or SNP5259.

In still another aspect, the present specification provides a non-transgenic corn plant comprising a synthetic mutation in a BR gene reducing the activity of the BR gene.

In another aspect, the present specification provides a modified corn plant comprising a non-transgene or non-transposon mediated mutation in a BR gene reducing the activity of the BR gene.

In another aspect, the present specification provides a brachytic corn plant comprising a dominant, non-transgenic BR mutant allele.

The present specification also provides a method for producing a semi-dwarf corn plant, the method comprising: (a) providing a guide RNA that recognizes a target site in a BR gene in a corn cell, where the guide RNA acts in association with an RNA-guided nuclease that creates a strand break at the target site, (b) generating a corn plant from the corn cell, and, (c) selecting the corn plant exhibiting semi-dwarf phenotype.

In another aspect, the present specification includes a CRISPR based genome editing system comprising Cas9 and a guide RNA, where the CRISPR based genome editing system reduces the activity of a BR gene.

The present specification further provides a method of cleaving a BR gene in a corn cell, comprising providing a guide RNA and an RNA-guided nuclease into the corn cell, where the guide RNA acts in association with the RNA-guided nuclease to create a strand break at a target site.

DETAILED DESCRIPTION

Definitions

Unless defined otherwise herein, terms are to be understood according to conventional usage by those of ordinary skill in the relevant art. Examples of resources describing many of the terms related to molecular biology used herein can be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2002; and Lewin, Genes IX, Oxford University Press: New York, 2007. The nomenclature for DNA bases as set forth at 37 C.F.R. § 1.822 is used.

Any references cited herein, including, e.g., all patents, published patent applications, and non-patent publications, are incorporated by reference in their entirety.

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

As used herein, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, "plant" refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present invention may be viable, nonviable, regenerable, and/or non-regenerable. A "propagule" may include any plant part that is capable of growing into an entire plant.

As used herein, a "corn plant" or "maize plant" refers to a plant of species Zea mays L and includes all plant varieties that can be bred with corn, including wild maize species.

As used herein, a "dwarf" plant refers to an atypically small plant. Generally, such a "dwarf plant" has a stature or height that is reduced from that of a control wild-type plant (e.g., a sibling plant comprising all other traits except the dwarf trait) by about 30%, 35%, 40%, 45%, 50%, 55%, 60% or greater.

As used herein, a "semi-dwarf plant" refers to a plant having a stature or height that is reduced from that of a control wild-type plant by about 5%, 10%, 15%, 20%, 25%, 30% or less. Generally, but not exclusively, such a dwarf plant is characterized by a reduced stem, stalk, or trunk length when compared to the control wild-type plant under comparable growth conditions. In one aspect, the stem, stalk, or trunk length of a modified corn plant comprising a non-naturally occurring mutation in a BR gene of the present disclosure is about 5%, 6%, 7%, 8%, 9%, 10%, 10%, 11%, 12%, 13%, 14%, 15%, 16%, 17%, 18%, 19%, 20%, 21%, 22%, 23%, 24%, 25%, 26%, 27%, 28%, 29%, or 30%, compared to that of a control plant not having the non-naturally occurring mutation in the BR gene under comparable growth conditions. As used herein, a "brachytic plant" refers to a plant showing a short stature due to a shortening of the internode length without a corresponding reduction in the number of internodes or the number and size of other organs including, but not limited to, leaves, ear and tassel. "Brachysm" refers to an abnormal variation of plants characterized by shortening of the internodes, without corresponding reductions of other plant parts. A "brachytic mutation" refers to a mutation in a BR gene that results in a brachytic plant.

As used herein, a "BR gene" refers to any brachytic gene in a plant, the mutation of which results in a brachytic plant. In one aspect, the BR gene is a BR1 gene. In another aspect, the BR gene is a BR2 gene. In still another aspect, the BR gene is a BR3 gene.

As used herein, "germplasm" refers to living sources of genetic material. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leaves, stems, pollen, or cells that can be cultured into a whole plant.

As used herein, a "transgenic plant" refers to a plant whose genome has been altered by the integration or insertion of a recombinant DNA molecule, construct or sequence. A transgenic plant includes an $R_0$ plant developed or regenerated from an originally transformed plant cell(s) as well as progeny transgenic plants in later generations or crosses from the $R_0$ transgenic plant.

As used herein, a "mutation" refers to the permanent alteration of the nucleotide sequence of the genome of an organism, the extrachromosomal DNA, or other genetic elements.

As used herein, the term "substitution mutation" refers to an exchange of a single nucleotide for another.

As used herein, the term "insertion" refers to the addition of one or more extra nucleotides into the DNA. Insertions in the coding region of a gene may alter splicing of the mRNA (splice site mutation), or cause a shift in the reading frame (frameshift), both of which can significantly alter the gene product.

As used herein, the term "deletion" refers to the removal of one or more nucleotides from the DNA. Like insertions, these mutations can alter the reading frame of the gene.

As used herein, the term "inversion" refers to reversing the orientation of a chromosomal segment.

As used herein, the term "duplication" refers to the creation of multiple copies of chromosomal regions, increasing the dosage of the genes located within them.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence.

For optimal alignment of sequences to calculate their percent identity, various pair-wise or multiple sequence alignment algorithms and programs are known in the art, such as ClustalW, etc., that may be used to compare the sequence identity or similarity between two or more nucleotide or protein sequences. Although other alignment and comparison methods are known in the art, the alignment and percent identity between two sequences (including the percent identity ranges described above) may be as determined by the ClustalW algorithm, See, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); and Larkin M A et al., "Clustal W and Clustal X version 2.0," *Bioinformatics* 23: 2947-48 (2007), the entire contents and disclosures of which are incorporated herein by reference.

As commonly understood in the art, the term "promoter" may generally refer to a DNA sequence that contains an RNA polymerase binding site, transcription start site, and/or TATA box and assists or promotes the transcription and expression of an associated transcribable polynucleotide sequence and/or gene (or transgene). A promoter may be synthetically produced, varied or derived from a known or naturally occurring promoter sequence or other promoter sequence. A promoter may also include a chimeric promoter comprising a combination of two or more heterologous sequences. A promoter of the present disclosure may thus include variants of promoter sequences that are similar in composition, but not identical to, other promoter sequence(s) known or provided herein. A promoter may be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter may also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed. The term "plant-expressible promoter" refers to a promoter that is able to initiate, assist, affect, cause, and/or promote the transcription and expression of its associated transcribable DNA sequence, coding sequence or gene in a plant cell or tissue.

The term "heterologous" in reference to a promoter is a promoter sequence having a different origin relative to its associated transcribable DNA sequence, coding sequence or gene (or transgene), and/or not naturally occurring in the plant species to be transformed. The term "heterologous" may refer more broadly to a combination of two or more DNA molecules or sequences, such as a promoter and an associated transcribable DNA sequence, coding sequence or gene, when such a combination is man-made and not normally found in nature.

The term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other. A recombinant polynucleotide or protein molecule, construct, etc., may comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., may also refer to a polynucleotide or protein molecule or sequence that has been genetically engineered and/or constructed outside of a cell. For example, a recombinant DNA molecule may comprise any suitable plasmid, vector, etc., and may include a linear or circular DNA molecule. Such plasmids, vectors, etc., may contain various maintenance elements including a prokaryotic origin of replication and selectable marker, as well as one or more transgenes or expression cassettes perhaps in addition to a plant selectable marker gene, etc. The term recombinant can also refer to an organism that harbors recombinant material, e.g., a plant that comprises a recombinant nucleic acid is considered a recombinant plant.

As used herein, "allele" refers to an alternative nucleic acid sequence at a particular locus; the length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. A favorable allele is the allele at a particular locus that confers, or contributes to, an agronomically desirable phenotype, or alternatively, is an allele that allows the identification of susceptible plants that can be removed from a breeding program or planting. A favorable allele of a marker is a marker allele that segregates with the favorable phenotype, or alternatively, segregates with susceptible plant phenotype, therefore providing the benefit of identifying disease prone plants. A favorable allelic form of a chromosome interval is a chromosome interval that includes a nucleotide sequence that contributes to superior agronomic performance at one or more genetic loci physically located on the chromosome interval.

As used herein, "crossed" or "cross" means to produce progeny via fertilization (e.g., cells, seeds or plants) and includes crosses between plants (sexual) and self-fertilization (selling).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the $F_1$ generation. The term "BC1" refers to the second use of the recurrent parent, "BC2" refers to the third use of the recurrent parent, and so on. In one aspect, a backcross is performed repeatedly, with a progeny individual of each successive backcross generation being itself backcrossed to the same parental genotype.

As used herein, "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome. A "haplotype" is the genotype of an individual at a plurality of genetic loci. Typically, the genetic loci described by a haplotype are physically and genetically linked, i.e., on the same chromosome interval.

As used herein, "locus" is a chromosome region where a polymorphic nucleic acid, trait determinant, gene, or marker is located. The loci of this disclosure comprise one or more polymorphisms in a population; e.g., alternative alleles are present in some individuals. As used herein, "allele" refers to an alternative nucleic acid sequence at a particular locus. The length of an allele can be as small as 1 nucleotide base, but is typically larger. For example, a first allele can occur on one chromosome, while a second allele occurs on a second homologous chromosome, e.g., as occurs for different chromosomes of a heterozygous individual, or between different homozygous or heterozygous individuals in a population. As used herein, a chromosome in a diploid plant is "hemizygous" when only one copy of a locus is present. For example, an inserted transgene is hemizygous when it only inserts into one sister chromosome (i.e., the second sister chromosome does not contain the inserted transgene).

The terms "phenotype," or "phenotypic trait" or "trait" refers to one or more trait of an organism. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, i.e., a "single gene trait." In other cases, a phenotype is the result of several genes.

"Operably linked" refers to the association of two or more nucleic acid elements in a recombinant DNA construct, e.g., as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g., by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression.

"Polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, a "vector," an "expression cassette," or a "cassette," is a polynucleotide or other molecule that transfers nucleic acids between cells. Vectors are often derived from plasmids, bacteriophages, or viruses and optionally comprise parts which mediate vector maintenance and enable its intended use. A "cloning vector" or "shuttle vector" or "sub cloning vector" contains operably linked parts that facilitate subcloning steps (e.g., a multiple cloning site containing multiple restriction endonuclease sites). The term "expression vector" as used herein refers to a vector comprising operably linked polynucleotide sequences that facilitate expression of a coding sequence in a particular host organism (e.g., a bacterial expression vector or a plant expression vector).

As used herein, a "yield" is the culmination of all agronomic traits as determined by the productivity per unit area of a particular plant product of commercial value. "Agronomic traits," include the underlying genetic elements of a given plant variety that contribute to yield over the course of growing season.

As used herein, "comparable growth conditions" refers to similar environmental conditions and/or agronomic practices for growing and making meaningful comparisons between two or more plant genotypes so that neither environmental conditions nor agronomic practices would contribute to, or explain, any differences observed between the two or more plant genotypes. Environmental conditions include, for example, light, temperature, water, humidity, and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp. 70-103.

As used herein, "selecting" or "selection" in the context of breeding refer to the act of picking or choosing desired individuals, normally from a population, based on certain pre-determined criteria.

The use of the term "polynucleotide" is not intended to limit the present disclosure to polynucleotides comprising DNA. Those of ordinary skill in the art will recognize that polynucleotides and nucleic acid molecules can comprise ribonucleotides and combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like.

As used herein, the term "polypeptide" refers to a chain of at least two covalently linked amino acids.

Description

BR2 Gene and Semi-Dwarf Phenotype

Brachytic corn mutants show a short stature due to a shortening of the internode length without a corresponding reduction in the number of internodes or the number and size of other organs, including the leaves, ear and tassel. See Pilu et al., *Molecular Breeding*, 20:83-91(2007). Three brachytic mutants brachytic1 (br1), brachytic2 (br2) and brachytic3

(br3) have been isolated. A maize brachytic mutant of particular agronomic potential is the recessive mutation br2, which results in the shortening of the internodes of the lower stalk with no obvious reduction in other plant organs. In addition, br2 lines exhibit an unusual stalk strength and tolerance to wind lodging, while the leaves are often darker and persist longer in the active green than those of the wild-type plants. The br2 phenotype is insensitive to treatment with GAs, auxins, brassinosteroids and cytokinins, suggesting that the biosynthesis of these hormones is not modified by the br2 mutation. Multani et al. identified the genomic sequence of the Br2 gene and deposited it under GenBank Accession No. AY366085. See Science, 302(5642) 81-84 (2003). Br2 was annotated to encode a putative protein similar to adenosine triphosphate (ATP)-binding cassette transporters of the multidrug resistant (MDR) class of P-glycoproteins (PGPs). As shown in FIG. 1, the BR2 gene contains 5 exons and 4 introns: Exon 1, Exon 2, Exon 3, Exon 4, Exon 5, triton 1, Intron 2, Intron 3, and Intron 4.

The present disclosure provides a corn plant comprising at least one non-natural BR mutation, wherein the corn plant exhibits a semi-dwarf phenotype compared to a control corn plant not comprising the non-natural BR mutation when grown under comparable conditions.

Natural BR gene mutations have been discovered to contribute to the brachytic or semi-dwarf phenotype in corn plants. The present disclosure provides a modified corn plant comprising a non-naturally occurring mutation in a BR gene, including a BR2 gene.

As used herein, a "natural mutation," a "naturally occurring mutation," or a "native" mutation, refers to a mutation as it occurs spontaneously in nature without any involvement of laboratory or experimental procedures or under the exposure to mutagens. Without being bound by scientific theory, a naturally-occurring mutation can arise from a variety of sources, including errors in DNA replication, spontaneous lesion, and transposable elements (or transposon).

The term "a non-natural mutation" or "a non-naturally occurring mutation" refers to a mutation not spontaneously occurred in nature but as a result of laboratory or experimental procedures or under the exposure to mutagens.

The present disclosure provides a modified corn plant comprising a non-naturally occurring mutation in a BR gene reducing the activity of the BR gene, wherein the mutation is not introduced via transposon.

As used herein, "modified", in the context of plants, seeds, plant components, plant cells, and plant genomes, refers to a state containing changes or variations from their natural or native state. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of Agrobacterium transformation or microprojectile bombardment), or a combination thereof.

As used herein, "transposon" refers to DNA sequences that can change its position within a genome, creating or reversing mutations and altering the cell's genome size.

In one aspect, the modified corn plant provided herein does not comprise a br2-23 brachytic mutation. As used herein, the term "br2-23 brachytic mutation" refers to a naturally occurring recessive mutation carrying an eight-nucleotide deletion in the coding region of the maize br2 gene concordant with the brachytic phenotype, as reported in Pilu et al., *Molecular Breeding*, 20: 83-91(2007), and Cassani et al., Plant Growth Regul., 64: 185-192(2011). These references are herein incorporated by reference in its entirety.

In one aspect, the modified corn plant of the present disclosure does not comprise SNP5259. As used herein, the term "SNP5259" refers to a naturally occurring single nucleotide polymorphism (SNP) in a maize plant height quantitative trait locus (QTL), qph1, which was validated as the causative mutation that reduces plant height and increases yield potential in maize. This was reported in Xing et al., *J. Exp. Bot.*, 66: 3791-802 (2015). This reference is herein incorporated by reference in its entirety.

In one aspect, the modified corn plant of the present disclosure does not comprise br2 brachytic polymorphism alleles identified by using a marker-assisted selection in maize, as reported in U.S. Application Publication No. 2016/0319375, herein incorporated by reference in its entirety, together with U.S. Provisional Application Nos. 62/180,430 and 62/153,831.

In one aspect, the modified corn plant of the present disclosure does not comprise any corn plants containing native BR2 mutant alleles. In one aspect, the modified corn plant of the present disclosure does not comprise a corn plant containing the native br2-MX mutant alleles, as described in Example 1 and shown in FIGS. 2 and 5A of the present disclosure.

In another aspect, the modified corn plant of the present disclosure does not comprise a br2-23 brachytic mutation, SNP5259, multiple br2 brachytic polymorphism alleles, br2-MX mutant alleles, or any other naturally-occurring or native mutation in a BR gene. In one aspect, the BR gene is a Br1 gene. In another aspect, the BR gene is a Br2 gene. In yet another aspect, the BR gene is a Br3 gene.

In one aspect, a plant described herein comprises a br2 mutation introduced via targeted genome editing to mimic a naturally occurring mutant br2 allele. In another aspect, a method described herein comprises targeted genome editing of a brachytic gene (e.g., BR2) in a desired inbred background to introduce a naturally occurring mutant br2 allele.

In one aspect, the present disclosure provides a non-transgenic corn plant comprising a synthetic mutation in a BR gene reducing the activity of the BR gene. As used herein, the term "synthetic mutation" refers to non-spontaneous mutation and occurs as a result of exposure to mutagens.

In another aspect, the present disclosure provides a modified corn plant comprising a non-transgene or non-transposon mediated mutation in a BR gene reducing the activity of the BR gene. As used herein, the term "transgene" refers to a recombinant DNA molecule, construct or sequence integrated or inserted into a genome, and thus altering the genome.

In one aspect, the modified corn plant comprising a non-naturally occurring substitution mutation in a BR gene. In another aspect, the modified corn plant comprising a non-naturally occurring insertion in a BR gene. In another aspect, the modified corn plant comprising a non-naturally occurring inversion in a BR gene. In yet another aspect, the modified corn plant comprising a non-naturally occurring deletion in a BR gene. In yet another aspect, the modified corn plant comprising a non-naturally occurring duplication in a BR gene.

The present disclosure further provides a modified corn plant comprising a non-naturally occurring insertion in a BR2 gene, where the insertion causes a truncation of the BR2 protein encoded by the BR2 gene. In one aspect, the insertion occurs within Exon 1 of the BR2 gene, where the insertion introduces premature stop codon. In another aspect, the insertion occurs within Exon 2 of the BR2 gene, where the insertion introduces premature stop codon. In another aspect, the insertion occurs within Exon 3 of the BR2 gene, where the insertion introduces premature stop codon. In another aspect, the insertion occurs within Exon 4 of the BR2 gene, where the insertion introduces premature stop codon. In another aspect, the insertion occurs within Exon 5 of the BR2 gene, where the insertion introduces premature stop codon. In another aspect, the insertion occurs within 3'UTR of the BR2 gene. In yet another aspect, the insertion occurs within 5'UTR of the BR2 gene.

In one aspect, the at least one non-natural BR or BR2 mutation is at least one insertion. In another aspect, the at least one insertion is a single nucleobase insertion. In one aspect, the single nucleobase is guanine. In another aspect, the single nucleobase is cytosine. In another aspect, the single nucleobase is adenine. In another aspect, the single nucleobase is thymine. In another aspect, the single nucleobase is uracil. In another aspect, a thymine is inserted between nucleotide number 5420 and 5421 according to the BR2 open reading frame to create a premature stop codon. In one aspect, the single nucleobase insertion is within Exon 1 of the BR2 gene. In another aspect, the single nucleobase insertion is within Exon 2 of the BR2 gene. In another aspect, the single nucleobase insertion is within Exon 3 of the BR2 gene. In another aspect, the single nucleobase insertion is within Exon 4 of the BR2 gene. In another aspect, the single nucleobase insertion is within Exon 5 of the BR2 gene. In another aspect, the single nucleobase insertion is within 3'UTR of the BR2 gene. In another aspect, the single nucleobase insertion is within 5'UTR of the BR2 gene. In another aspect, the single nucleobase insertion is within a promoter of the BR2 gene. In another aspect, the single nucleobase insertion is within Intron 1 of the BR2 gene. In another aspect, the single nucleobase insertion is within Intron 2 of the BR2 gene. In another aspect, the single nucleobase insertion is within Intron 3 of the BR2 gene. In another aspect, the single nucleobase insertion is within Intron 4 of the BR2 gene.

In another aspect, the at least one insertion is within Exon 1 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Exon 2 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Exon 3 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Exon 4 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Exon 5 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within 3'UTR of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within 5'UTR of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within a promoter of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Intron 1 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Intron 2 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Intron 3 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the at least one insertion is within Intron 4 of the BR2 gene, where the at least one insertion comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In one aspect, the at least one non-natural BR or BR2 mutation is at least one substitution. In another aspect, the at least one substitution is within Exon 1 of the BR2 gene. In another aspect, the at least one substitution is within Exon 2 of the BR2 gene. In another aspect, the at least one substitution is within Exon 3 of the BR2 gene. In another aspect, the at least one substitution is within Exon 4 of the BR2 gene. In another aspect, the at least one substitution is within Exon 5 of the BR2 gene. In another aspect, the at least one substitution is within 3'UTR of the BR2 gene. In another aspect, the at least one substitution is within 5'UTR of the BR2 gene. In another aspect, the at least one substitution is within a promoter of the BR2 gene. In another aspect, the at least one substitution is within Intron 1 of the BR2 gene. In another aspect, the at least one substitution is within Intron 2 of the BR2 gene. In another aspect, the at least one substitution is within Intron 3 of the BR2 gene. In another aspect, the at least one substitution is within Intron 4 of the BR2 gene.

In one aspect, the at least one non-natural BR or BR2 mutation is at least one deletion. In another aspect, the at least one deletion is within Exon 1 of the BR2 gene. In another aspect, the at least one deletion is within Exon 2 of the BR2 gene. In another aspect, the at least one deletion is within Exon 3 of the BR2 gene. In another aspect, the at least one deletion is within Exon 4 of the BR2 gene. In another aspect, the at least one deletion is within Exon 5 of the BR2 gene. In another aspect, the at least one deletion is within 3'UTR of the BR2 gene. In another aspect, the at least one deletion is within 5'UTR of the BR2 gene. In another aspect, the at least one deletion is within a promoter of the BR2 gene. In another aspect, the at least one deletion is within Intron 1 of the BR2 gene. In another aspect, the at least one deletion is within Intron 2 of the BR2 gene. In another aspect, the at least one deletion is within Intron 3 of the BR2 gene. In another aspect, the at least one deletion is within Intron 4 of the BR2 gene.

In one aspect, the at least one non-natural BR or BR2 mutation is at least one duplication. In another aspect, the at least one duplication is within Exon 1 of the BR2 gene. In another aspect, the at least one duplication is within Exon 2 of the BR2 gene. In another aspect, the at least one duplication is within Exon 3 of the BR2 gene. In another aspect, the at least one duplication is within Exon 4 of the BR2 gene. In another aspect, the at least one duplication is within Exon 5 of the BR2 gene. In another aspect, the at least one duplication is within 3'UTR of the BR2 gene. In another aspect, the at least one duplication is within 5'UTR of the BR2 gene. In another aspect, the at least one duplication is within a promoter of the BR2 gene. In another aspect, the at least one duplication is within Intron 1 of the BR2 gene. In another aspect, the at least one duplication is within Intron 2 of the BR2 gene. In another aspect, the at least one duplication is within Intron 3 of the BR2 gene. In another aspect, the at least one duplication is within Intron 4 of the BR2 gene.

Genome Editing

Given that suppression of BR genes in corn produces plants having a shorter plant height, increased stalk diameter, and increased resistance to lodging, the present inventors further propose that expression of the BR genes may be reduced or eliminated through genome editing to provide these beneficial traits to corn or other monocot or cereal plants.

As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

As used herein, "editing" or "genome editing" refers to targeted mutagenesis, insertion, deletion, or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence.

Genome editing or targeted editing can be effected via the use of one or more site-specific nucleases. Site-specific nucleases can induce a double-stranded break (DSB) at a target site of a genome sequence that is then repaired by the natural processes of either homologous recombination (HR) or non-homologous end-joining (NHEJ). Sequence modifications, such as insertions, deletions, can occur at the DSB locations via NHEJ repair. HR can be used to integrate a donor nucleic acid sequence into a target site. If two DSBs flanking one target region are created, the breaks can be repaired via NHEJ by reversing the orientation of the targeted DNA (also referred to as an "inversion").

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In one aspect, a vector comprises in cis a cassette encoding a site-specific nuclease and a donor molecule such that when contacted with the genome of a cell, the site-specific nuclease enables site-specific integration of the donor molecule. In one aspect, a first vector comprises a cassette encoding a site-specific nuclease and a second vector comprises a donor molecule such that when contacted with the genome of a cell, the site-specific nuclease provided in trans enables site-specific integration of the donor molecule.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In one aspect, a method provided herein comprises the use of one or more, two or more, three or more, four or more, or five or more site-specific nucleases to induce one, two, three, four, five, or more than five DSBs at one, two, three, four, five, or more than five target sites.

In one aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to introduce a mutation, or generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, an RNA-guided nuclease provided herein is selected from the group consisting of a Cas9 or a Cpf1. In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

Recombinases

In an aspect, a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. The Flp-FRT site-directed recombination system comes from the 2 µ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

ZFNs

ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In one aspect, a method and/or composition provided herein comprises one or more, two or more, three or more, four or more, or five or more ZFNs in another aspect, a ZFN provided herein is capable of generating a targeted DSB. In one aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

Meganucleases

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In one aspect, a method and/or composition provided herein comprises one or more, two or more, three or more, four or more, or five or more meganucleases. In another aspect, a meganuclease provided herein is capable of generating a targeted DSB. In one aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI and FokI, AlwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. PLoS One. 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications*. 4: 1762).

The relationship between amino acid sequence and DNA recognition of the TALE binding domain allows for designable proteins. Software programs such as DNAWorks can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In one aspect, a method and/or composition provided herein comprises one or more, two or more, three or more, four or more, or five or more TALENs. In another aspect, a TALEN provided herein is capable of generating a targeted DSB. In one aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

CRISPR/Cas9

A CRISPR/Cas9 system or a CRISPR/Cpf1 system are alternatives to the FokI-based methods ZFN and TALEN. In one aspect, a genome editing system provided herein comprises a CRISPR system. The CRISPR systems are based on RNA-guided engineered nucleases that use complementary base pairing to recognize DNA sequences at target sites.

In an aspect, a vector provided herein can comprise any combination of a nucleic acid sequence encoding a RNA-guided nuclease.

While not being limited by any particular scientific theory, CRISPR/Cas nucleases are part of the adaptive immune system of bacteria and archaea, protecting them against invading nucleic acids such as viruses by cleaving target DNA in a sequence-dependent manner. The immunity is acquired by the integration of short fragments of the invading DNA, known as spacers, between ~20 nucleotide long CRISPR repeats at the proximal end of a CRISPR locus (a CRISPR array). A well described Cas protein is the Cas9 nuclease (also known as Csn1), which is part of the Class 2, type II CRISPR/Cas system in *Streptococcus pyogenes*. See Makarova et al. *Nature Reviews Microbiology* (2015) doi: 10.1038/nrmicro3569. Cas9 comprises an RuvC-like nuclease domain at its amino terminus and an HNH-like nuclease domain positioned in the middle of the protein. Cas9 proteins also contain a PAM-interacting (PI) domain, a recognition lobe (REC), and a BH domain. The Cpf1 nuclease, another type II system, acts in a similar manner to Cas9, but Cpf1 does not require a tracrRNA. See Cong et al. *Science* (2013) 339: 819-823; Zetsche et al., *Cell* (2015) doi: 10.1016/j.cell.2015.09.038; U.S. Patent Publication No. 2014/0068797; U.S. Patent Publication No. 2014/0273235; U.S. Patent Publication No. 2015/0067922; U.S. Pat. Nos. 8,697,359; 8,771,945; 8,795,965; 8,865,406; 8,871,445; 8,889,356; 8,889,418; 8,895,308; and 8,906,616, each of which is herein incorporated by reference in its entirety.

When Cas9 or Cpf1 cleaves targeted DNA, endogenous double stranded break (DSB) repair mechanisms are activated. DSBs can be repaired via non-homologous end joining, which can incorporate insertions or deletions (indels) into the targeted locus. If two DSBs flanking one target region are created, the breaks can be repaired by reversing the orientation of the targeted DNA. Alternatively, if a donor polynucleotide with homology to the target DNA sequence is provided, the DSB may be repaired via homology-directed repair. This repair mechanism allows for the precise integration of a donor polynucleotide into the targeted DNA sequence.

While not being limited by any particular scientific theory, in Class 2, type II CRISPR/Cas systems, CRISPR arrays, including spacers, are transcribed during encounters with recognized invasive DNA and are processed into small interfering CRISPR RNAs (crRNAs), which are approximately 40 nucleotides in length. The crRNAs hybridize with trans-activating crRNAs (tracrRNAs) to activate and guide the Cas9 nuclease to a target site. Nucleic acid molecules provided herein can combine a crRNA and a tracrRNA into one nucleic acid molecule in what is herein referred to as a "single-chain guide RNA (sgRNA)." A prerequisite for cleavage of the target site is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA. Therefore, in an aspect utilizing Cpf1 a sgRNA may be replaced by a crRNA.

In one aspect, a method and/or composition provided herein comprises one or more, two or more, three or more, four or more, or five or more Cas9 nucleases. In one aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In one aspect, a method and/or composition provided herein comprises one or more, two or more, three or more, four or more, or five or more Cpf1 nucleases. In one aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

In one aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In one aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In one aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof, an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1. In another aspect, an RNA-guided nuclease provided herein comprises Cas9. In one aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In one aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, TtAgo, PfAgo, and NgAgo.

Transformation

According to aspects of the present disclosure, methods are provided for transforming a cell, tissue or explant with a recombinant DNA molecule or construct comprising a transcribable DNA sequence or transgene operably linked to a promoter to produce a transgenic or genome edited cell. According to other aspects of the present disclosure, methods are provided for transforming a plant cell, tissue or explant with a recombinant DNA molecule or construct comprising a transcribable DNA sequence or transgene operably linked to a plant-expressible promoter to produce a transgenic or genome edited plant or plant cell.

Numerous methods for transforming chromosomes or plastids in a plant cell with a recombinant DNA molecule or construct are known in the art, which may be used according to methods of the present disclosure to produce a transgenic plant cell and plant. Any suitable method or technique for transformation of a plant cell known in the art may be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods may be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA are found in U.S. Pat. Nos. 5,550,318; 5,538,880; 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

Alternatively, the nucleotide sequences of the disclosure can be introduced into an organism and allowed to undergo recombination with homologous regions of the organism's genome. Such homologous recombination approaches are well known to those of ordinary skill in the art and can be used to stably incorporate sequences of the disclosure into an organism. Further, such strategies can be used to introduce "knockout mutations" into a specific gene of an organism that shares substantial homology to the sequences of the disclosure. A knockout mutation is any mutation in the sequence of a gene that eliminates or substantially reduces the function or the level of the product encoded by the gene. Methods involving transformation of an organism followed by homologous recombination to stably integrate the sequences of the disclosure into the genome organism are encompassed by the disclosure. The disclosure is particularly directed to methods where sequences of the disclosure are utilized to alter the growth of an organism. Such methods encompass use of the sequences of the disclosure to interfere with the function or synthesis of a P-glycoprotein that controls growth of an organism.

The cells that have been transformed may be grown into plants in accordance with conventional ways. See, for example, McCormick et al. (1986) Plant Cell Reports 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, all of which are incorporated herein by reference. Transformed explants, cells or tissues may be subjected to additional culturing steps, such as callus induction, selection, regeneration, etc., as known in the art. Transformed cells, tissues or explants containing a recombinant DNA insertion may be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction.

Transgenic plants may be further crossed to themselves or other plants to produce transgenic seeds and progeny. A transgenic plant may also be prepared by crossing a first plant comprising the recombinant DNA sequence or transformation event with a second plant lacking the insertion. For example, a recombinant DNA construct or sequence may be introduced into a first plant line that is amenable to transformation, which may then be crossed with a second plant line to introgress the recombinant DNA construct or sequence into the second plant line. Progeny of these crosses can be further back crossed into the more desirable line multiple times, such as through 6 to 8 generations or back crosses, to produce a progeny plant with substantially the same genotype as the original parental line but for the introduction of the recombinant DNA construct or sequence.

A plant, cell, or explant provided herein may be of an elite variety or an elite line. An elite variety or an elite line refers to any variety that has resulted from breeding and selection for superior agronomic performance. A plant, cell, or explant provided herein may be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties.

A recombinant DNA molecule or construct of the present disclosure may comprise or be included within a DNA transformation vector for use in transformation of a target plant cell, tissue or explant. Such a transformation vector of the present disclosure may generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs. For Agrobacterium-mediated transformation, the transformation vector may comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgR_NA(s) or crRNA(s) would be located between the left and right borders of the T-DNA, perhaps along with an additional transgene(s) or expression cassette(s), such as a plant selectable marker transgene and/or other gene(s) of agronomic interest that may confer a trait or phenotype of agronomic interest to a plant. According to alternative aspects, the transcribable DNA sequence, transgene or expression cassette encoding at least one site-specific nuclease, any necessary sgRNAs or crRNAs, and the plant selectable marker transgene (or other gene of agronomic interest) may be present in separate T-DNA segments on the same or different recombinant DNA molecule(s), such as for co-transformation. A transformation vector or construct may further comprise prokaryotic maintenance elements, which for Agrobacterium-mediated transformation may be located in the vector backbone outside of the T-DNA region(s).

A plant selectable marker transgene in a transformation vector or construct of the present disclosure may be used to assist in the selection of transformed cells or tissue due to the presence of a selection agent, such as an antibiotic or herbicide, wherein the plant selectable marker transgene provides tolerance or resistance to the selection agent. Thus, the selection agent may bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or Cp4-EPSPS). Plant screenable marker genes may also be used, which provide an ability to visually screen for transformants, such as luciferase or green fluorescent protein (GFP), or a gene expressing a beta glucuronidase or uidA gene (GUS) for which various chromogenic substrates are known. In one aspect, a vector or polynucleotide provided herein comprises at least one marker gene selected from the group consisting of nptII, aph IV, aadA, aac3, aacC4, bar, pat, DMO, EPSPS, aroA, GFP, and GUS.

According to aspects of the present disclosure, methods for transforming a plant cell, tissue or explant with a recombinant DNA molecule or construct may further include site-directed or targeted integration using site-specific nucleases. According to these methods, a portion of a recombinant DNA donor molecule (i.e., an insertion sequence) may be inserted or integrated at a desired site or locus within a genome. The insertion sequence of the donor template may comprise a transgene or construct, such as a small designed element or a tissue-specific promoter. The donor molecule may also have one or two homology arms flanking the insertion sequence to promote the targeted insertion event through homologous recombination and/or homology-directed repair. Thus, a recombinant DNA molecule of the present disclosure may further include a donor template for site-directed or targeted integration of a transgene or construct, such as a transgene or transcribable DNA sequence encoding a small designed element or a tissue-specific promoter into a genome.

Some aspects of the present disclosure relate to screening cells or plants for targeted edits and selecting cells or plants comprising targeted edits. Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Any method known in the art for suppression of a target gene may be used to suppress BR gene(s) according to aspects of the present disclosure including expression of antisense RNAs, double stranded RNAs (dsRNAs) or inverted repeat RNA sequences, or via co-suppression or RNA intereference (RNAi) through expression of small interfering RNAs (siRNAs), short hairpin RNAs (shRNAs), trans-acting siRNAs (ta-siRNAs), or micro RNAs (miRNAs). Furthermore, sense and/or antisense RNA molecules may be used that target the non-coding genomic sequences or regions within or near a gene to cause silencing of the gene. Accordingly, any of these methods may be used for the targeted suppression of an endogenous BR gene(s) in a tissue-specific or tissue-preferred manner. See, e.g., U.S. Patent Application Publication Nos. 2009/0070898, 2011/0296555, and 2011/0035839, the contents and disclosures of which are incorporated herein by reference.

The term "suppression" as used herein, refers to a lowering, reduction or elimination of the expression level of a mRNA and/or protein encoded by a target gene in a plant, plant cell or plant tissue at a given stage of plant development, as compared to the expression level of such target mRNA and/or protein in a wild-type or control plant, cell or tissue at the same stage of plant development. According to aspects of the present disclosure, a modified or transgenic plant provided herein comprises a BR expression level that is reduced by at least 5%, at least 10%, at least 20%, at least 25%, at least 30%, at least 40%, at least 50%, at least 60%, at least 70%, at least 75%, at least 80%, at least 90%, or 100% as compared to a control plant. According to aspects of the present disclosure, a modified or transgenic plant provided herein comprises a BR expression level that is reduced by 5%-20%, 5%-25%, 5%-30%, 5%-40%, 5%-40%, 5%-50%, 5%-60%, 5%-70%, 5%-75%, 5%-80%, 5%-90%, 5%-100%, 75%-100%, 50-100%, 50%-90%, 50%-75%, 25%-75%, 30%-80%, pr 10%-75% as compared to a control plant.

Method for Producing a Semi-Dwarf Corn Plant

Also provided in the present disclosure is a method for producing a semi-dwarf corn plant comprising providing a guide RNA that recognizes a target site in a BR gene in a corn cell, wherein the guide RNA acts in association with an RNA-guided nuclease that creates a strand break at the target site; generating a corn plant from the corn cell; and selecting the corn plant exhibiting semi-dwarf phenotype.

As used herein, the term "a guide RNA" or "a gRNA" is a short RNA sequence comprising (1) a scaffold RNA sequence necessary for binding with an RNA-guided nuclease, and (2) an RNA sequence complementary to a target sequence or a target site. In one aspect, the scaffold RNA sequence is as set forth in SEQ ID NO: 5. In another aspect, the target sequences for BR2 gene are as set forth in SEQ ID NOs: 7-17.

In one aspect, the gRNA comprises a sequence as set forth in SEQ ID NO: 6. In one aspect, the gRNA comprises a sequence at least 90%, at least 91%, at least 92%, at least 93%, at least 94%, at least 95%, at least 96%, at least 97%, at least 98%, at least 99%, or 100% identical to a nucleotide sequence as set forth in SEQ ID NO: 6.

As used herein, an "RNA-guided nuclease" refers to an RNA-guided DNA endonuclease associated with the CRISPR system. Non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof. In one aspect, the RNA-guided nuclease is Cas9. In one aspect, the RNA-guided nuclease comprises a nucleotide sequence at least 70%, at least 75%, at least 80%, at least 85%, at least 90%, at least 95%, at least 96%, at least 97%, at least 98%, at least 99% or 100% identical to a nucleotide sequence as set forth in SEQ ID NO: 1. In another aspect, the RNA-guided nuclease comprises an amino acid sequence at least 70%, at least 75%, at least 80%, at least 85%, at least 90%, at least 95%, at least 96%, at least 97%, at least 98%, at least 99% or 100% sequence identity to a polypeptide sequence as set forth in SEQ ID NO: 2. In one aspect, the RNA-guided nuclease comprises the N and C terminal nuclear localization sequences (NLS). In one aspect, the N terminal NLS is located at nucleotide positions 4 to 33 of SEQ ID NO: 1, and the C terminal NLS is located at nucleotide positions 3586 to 3615 of SEQ ID NO: 1.

As used herein, the term "a target site" or "a target sequence" refers to a location of a polynucleotide sequence that is bound to and cleaved by a site-specific nuclease introducing a strand break into the nucleic acid backbone. In one aspect, the strand break is a double stranded break. The target site is present immediately upstream of a 2-6 base pair DNA sequence, also known as a Protospacer Adjacent Motif (PAM). In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that is flanked by two or more target sites. Without being limiting, in some aspects a target region can be subject to deletion or inversion. As used herein, "flanked" when used to describe a target region, refers to two or more target sites physically surrounding the target region, with one target site on each side of the target region.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

In one aspect, the target site is a BR2 gene. In another aspect, the target site is within Exon 1 of the BR2 gene. In another aspect, the target site is within Exon 2 of the BR2 gene. In another aspect, the target site is within Exon 3 of the BR2 gene. In another aspect, the target site is within Exon 4 of the BR2 gene. In another aspect, the target site is within Exon 5 of the BR2 gene. In another aspect, the target site is within 3'UTR of the BR2 gene. In another aspect, the target site is within 5'UTR of the BR2 gene. In another aspect, the target site is within a promoter of the BR2 gene. In another aspect, the target site is within Intron 1 of the BR2 gene. In another aspect, the target site is within Intron 2 of the BR2 gene. In another aspect, the target site is within Intron 3 of the BR2 gene. In another aspect, the target site is within Intron 4 of the BR2 gene.

In one aspect, the target site comprises a nucleotide sequence as set forth in SEQ ID NO: 7. In another aspect, the target site comprises a nucleotide sequence as set forth in SEQ ID NO: 8. In another aspect, the target site comprises a nucleotide sequence as set forth in SEQ ID NO: 9. In another aspect, the target site comprises a nucleotide sequence as set forth in SEQ ID NO: 10. In another aspect, the target site comprises a nucleotide sequence as set forth in SEQ ID NO: 11. In another aspect, the target site comprises a nucleotide sequence as set forth in SEQ ID NO: 12. In another aspect, the target site comprises a nucleotide sequence as set forth in SEQ ID NO: 13. In another aspect, the target site comprises a nucleotide sequence as set forth in SEQ ID NO: 14. In another aspect, the target site comprises a nucleotide sequence as set forth in SEQ ID NO: 15. In another aspect, the target site comprises a nucleotide sequence as set forth in SEQ ID NO: 16. In another aspect, the target site comprises a nucleotide sequence as set forth in SEQ ID NO: 17.

As used herein a "donor molecule" is defined as a nucleic acid sequence that has been selected for site directed, targeted insertion into a genome. In one aspect, a targeted editing technique provided herein comprises the use of one or more, two or more, three or more, four or more, or five or more donor molecules. A donor molecule provided herein can be of any length. For example, a donor molecule provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length. A donor molecule can comprise one or more genes that encode actively transcribed and/or translated gene sequences. Such transcribed sequences can encode a protein or a non-coding RNA. In some aspects, the donor molecule can comprise a polynucleotide sequence which does not comprise a functional gene or an entire gene (i.e., the donor molecule may simply comprise regulatory sequences such as a promoter), or may not contain any identifiable gene expression elements or any actively transcribed gene sequence. Further, the donor molecule can be linear or circular, and can be single-stranded or double-stranded. It can be delivered to the cell as naked nucleic acid, as a complex with one or more delivery agents (e.g., liposomes, poloxamers, T-strand encapsulated with proteins, etc.) or contained in a bacterial or viral delivery vehicle, such as, for example, *Agrobacterium* tumefriciens or a geminivirus, respectively. In another aspect, a donor molecule provided herein is operably linked to a promoter. In a still further aspect, a donor molecule provided herein is transcribed into RNA. In another aspect, a donor molecule provided herein is not operably linked to a promoter.

In an aspect, a donor molecule provided herein can comprise at least one, at least two, at least three, at least four, at least five, at least six, at least seven, at least eight, at least nine, or at least ten genes. In an aspect, a donor molecule provided herein comprises no genes. Without being limiting, a gene provided herein can include an insecticidal resistance gene, an herbicide tolerance gene, a nitrogen use efficiency gene, a water use efficiency gene, a nutritional quality gene, a DNA binding gene, a selectable marker gene, an RNAi construct, a site-specific genome modification enzyme gene, a single guide RNA of a CRISPR/Cas9 system, a geminivirus based expression cassette, or a plant viral expression vector system. In one aspect, a donor molecule comprises a polynucleotide that encodes a promoter. In another aspect, a donor molecule provided herein comprises a polynucleotide that encodes a tissue-specific or tissue-preferred promoter. In still another aspect, a donor molecule provided herein comprises a polynucleotide that encodes a constitutive promoter. In another aspect, a donor molecule provided herein comprises a polynucleotide that encodes an inducible promoter. In another aspect, a donor molecule comprises a polynucleotide that encodes a structure selected from the group consisting of a leader, an enhancer, a transcriptional start site, a 5'-UTR, an exon, an intron, a 3'-UTR, a polyadenylation site, a transcriptional termination site, a promoter, a full-length gene, a partial gene, a gene, or a non-coding RNA.

Any site or locus within the genome of a plant may potentially be chosen for site-directed integration of a donor sequence. For site-directed integration, a double-strand break (DSB) or nick may first be made at a selected genomic locus with a site-specific nuclease, such as, for example, a zinc-finger nuclease, an engineered or native meganuclease, a TALE-endonuclease, or an RNA-guided endonuclease (e.g., Cas9 or Cpf1). Any method known in the art for site-directed integration may be used. In the presence of a donor sequence, the DSB or nick may then be repaired by homologous recombination between the homology arm(s) of the donor template and the plant genome, or by non-homologous end joining (NHEJ), resulting in site-directed integration of the donor sequence into the plant genome to create the targeted insertion event at the site of the DSB or nick. Thus, site-specific insertion or integration of a transgene or construct may be achieved.

In one aspect, a sequence can be inserted into a double-stranded break created by a CRISPR based genome editing system without the presence of a donor sequence. In one aspect, a single base insertion into a double-stranded break created by a CRISPR based genome editing system can be achieved via non-homologous end joining (NHEJ) without a donor sequence. In another aspect, a single base can be inserted into a BR2 gene via the CRISPR based genome editing system of the present disclosure. In one aspect, a single base can be inserted in Exon 1 of BR2 gene, thus creating a premature stop codon. In another aspect, a single base can be inserted in Exon 2 of BR2 gene, thus creating a premature stop codon. In yet another aspect, a single base can be inserted in Exon 3 of BR2 gene, thus creating a premature stop codon. In still another aspect, a single base can be inserted in Exon 4 of BR2 gene, thus creating a premature stop codon. In another aspect, a single base can be inserted in Exon 5 of BR2 gene, thus creating a premature stop codon.

In another aspect, a donor sequence can be inserted or integrated into a strand break created by the guide RNA acting in association with the RNA-guided nucleases. In one aspect, the strand break is a double stranded break (DSB). The donor sequence may comprise a transgene or construct, such as a non-coding RNA molecule that targets a BR gene. In one aspect, the donor sequence introduces a premature stop codon into a BR2 gene. In one aspect, the premature stop codon is inserted within Exon 1 of the BR2 gene. In another aspect, the premature stop codon is inserted within Exon 2 of the BR2 gene. In another aspect, the premature stop codon is inserted within Exon 3 of the BR2 gene. In another aspect, the premature stop codon is inserted within Exon 4 of the BR2 gene. In another aspect, the premature stop codon is inserted within Exon 5 of the BR2 gene.

According to one aspect of the present disclosure, the method for producing a semi-dwarf corn plant creates at least one non-natural BR or BR2 mutation further comprising integrating into the strand break a sequence. In one aspect, the sequence is integrated into the BR or BR2 gene via non-homologous end joining (NHEJ). In one aspect, the sequence is a single guanine. In another aspect, the sequence is a single cytosine. In another aspect, the sequence is a single adenine. In another aspect, the sequence is a single thymine. In another aspect, the sequence is a single uracil. In another aspect, a thymine is inserted between nucleotide number 5420 and 5421 according to the BR2 open reading frame to create a premature stop codon.

In one aspect, the single nucleotide is integrated in Exon 1 of the BR2 gene. In another aspect, the single nucleotide is integrated in Exon 2 of the BR2 gene. In another aspect, the single nucleotide is integrated in Exon 3 of the BR2 gene. In another aspect, the single nucleotide is integrated in Exon 4 of the BR2 gene. In another aspect, the single nucleotide is integrated in Exon 5 of the BR2 gene. In another aspect, the single nucleotide is integrated in 3'UTR of the BR2 gene. In another aspect, the single nucleotide is integrated in 5'UTR of the BR2 gene. In another aspect, the single nucleotide is integrated in a promoter of the BR2 gene. In another aspect, the single nucleotide is integrated in Intron 1 of the BR2 gene. In another aspect, the single nucleotide is integrated in Intron 2 of the BR2 gene. In another aspect, the single nucleotide is integrated in Intron 3 of the BR2 gene. In another aspect, the single nucleotide is integrated in Intron 4 of the BR2 gene.

In one aspect, the sequence comprises at least 2 nucleotides. In another aspect, the sequence comprises at least 3 nucleotides. In another aspect, the sequence comprises at least 4 nucleotides. In another aspect, the sequence comprises at least 5 nucleotides. In another aspect, the sequence comprises at least 6 nucleotides. In another aspect, the sequence comprises at least 7 nucleotides. In another aspect, the sequence comprises at least 8 nucleotides. In another aspect, the sequence comprises at least 9 nucleotides. In another aspect, the sequence comprises at least 10 nucleotides. In one aspect, the sequence is integrated within Exon 1 of the BR2 gene. In another aspect, the sequence is integrated within Exon 2 of the BR2 gene. In another aspect, the sequence is integrated within Exon 3 of the BR2 gene. In another aspect, the sequence is integrated within Exon 4 of the BR2 gene. In another aspect, the sequence is integrated within Exon 5 of the BR2 gene. In another aspect, the sequence is integrated within 3'UTR of the BR2 gene. In another aspect, the sequence is integrated within 5'UTR of the BR2 gene. In another aspect, the sequence is integrated within a promoter of the BR2 gene. In another aspect, the sequence is integrated within Intron 1 of the BR2 gene. In another aspect, the sequence is integrated within Intron 2 of the BR2 gene. In another aspect, the sequence is integrated within Intron 3 of the BR2 gene. In another aspect, the sequence is integrated within Intron 4 of the BR2 gene.

In another aspect, the sequence is integrated into the BR or BR2 gene by a donor sequence via homologous recombination (FIR). In one aspect, the sequence is a single nucleotide. In one aspect, the sequence is a single guanine. In another aspect, the sequence is a single cytosine. In another aspect, the sequence is a single adenine. In another aspect, the sequence is a single thymine. In another aspect, the sequence is a single uracil. In another aspect, a thymine is inserted between nucleotide number 5420 and 5421 according to the BR2 open reading frame to create a premature stop codon. In one aspect, the single nucleotide is integrated in Exon 1 of the BR2 gene. In another aspect, the single nucleotide is integrated in Exon 2 of the BR2 gene. In another aspect, the single nucleotide is integrated in Exon 3 of the BR2 gene. In another aspect, the single nucleotide is integrated in Exon 4 of the BR2 gene. In another aspect, the single nucleotide is integrated in Exon 5 of the BR2 gene. In another aspect, the single nucleotide is integrated in 3'UTR of the BR2 gene. In another aspect, the single nucleotide is integrated in 5' UTR of the BR2 gene. In another aspect, the single nucleotide is integrated in a promoter of the BR2 gene. In another aspect, the single nucleotide is integrated in Intron 1 of the BR2 gene. In another aspect, the single nucleotide is integrated in Intron 2 of the BR2 gene. In another aspect, the single nucleotide is integrated in Intron 3 of the BR2 gene. In another aspect, the single nucleotide is integrated in Intron 4 of the BR2 gene.

In one aspect, the sequence comprises at least 2 nucleotides and is integrated within the BR or BR2 gene by a donor sequence.

In another aspect, the sequence is integrated within Exon 1 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Exon 2 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Exon 3 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Exon 4 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Exon 5 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within 3'UTR of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within 5' UTR of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within a promoter of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Intron 1 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Intron 2 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Intron 3 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In another aspect, the sequence is integrated within Intron 4 of the BR2 gene, where the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

In one aspect, the method for producing a semi-dwarf corn plant further comprises integrating into the strand break at least one substitution, at least one inversion, at least one deletion, at least one duplication, or a combination thereof.

In another aspect, the at least one substitution is within Exon 1 of the BR2 gene. In another aspect, the at least one substitution is within Exon 2 of the BR2 gene. In another aspect, the at least one substitution is within Exon 3 of the BR2 gene. In another aspect, the at least one substitution is within Exon 4 of the BR2 gene. In another aspect, the at least one substitution is within Exon 5 of the BR2 gene. In another aspect, the at least one substitution is within 3'UTR of the BR2 gene. In another aspect, the at least one substitution is within 5'UTR of the BR2 gene. In another aspect, the at least one substitution is within a promoter of the BR2 gene. In another aspect, the at least one substitution is within Intron 1 of the BR2 gene. In another aspect, the at least one substitution is within Intron 2 of the BR2 gene. In another aspect, the at least one substitution is within Intron 3 of the BR2 gene. In another aspect, the at least one substitution is within Intron 4 of the BR2 gene.

In another aspect, the at least one deletion is within Exon 1 of the BR2 gene. In another aspect, the at least one deletion is within Exon 2 of the BR2 gene. In another aspect, the at least one deletion is within Exon 3 of the BR2 gene. In another aspect, the at least one deletion is within Exon 4 of the BR2 gene. In another aspect, the at least one deletion is within Exon 5 of the BR2 gene. In another aspect, the at least one deletion is within 3'UTR of the BR2 gene. In another aspect, the at least one deletion is within 5'UTR of the BR2 gene. In another aspect, the at least one deletion is within a promoter of the BR2 gene. In another aspect, the at least one deletion is within Intron 1 of the BR2 gene. In another aspect, the at least one deletion is within Intron 2 of the BR2 gene. In another aspect, the at least one deletion is within Intron 3 of the BR2 gene. In another aspect, the at least one deletion is within Intron 4 of the BR2 gene.

In another aspect, the at least one duplication is within Exon 1 of the BR2 gene. In another aspect, the at least one duplication is within Exon 2 of the BR2 gene. In another aspect, the at least one duplication is within Exon 3 of the BR2 gene. In another aspect, the at least one duplication is within Exon 4 of the BR2 gene. In another aspect, the at least one duplication is within Exon 5 of the BR2 gene. In another aspect, the at least one duplication is within 3'UTR of the BR2 gene. In another aspect, the at least one duplication is within 5'UTR of the BR2 gene. In another aspect, the at least one duplication is within a promoter of the BR2 gene. In another aspect, the at least one duplication is within Intron 1 of the BR2 gene. In another aspect, the at least one duplication is within Intron 2 of the BR2 gene. In another aspect, the at least one duplication is within Intron 3 of the BR2 gene. In another aspect, the at least one duplication is within Intron 4 of the BR2 gene.

Semi-Dwarf Phenotype

Brachytic, dwarf, or semi-dwarf corn disclosed herein may have characteristics that make it suitable for grain and forage production, especially, production in short-season environments. In particular, the limited heat units in short-season environments reduce grain yield and lessen the probability of the crop reaching physiological maturity in a given year. The disclosed brachytic, dwarf, or semi-dwarf corn plants require fewer heat units (e.g., required 10%) than conventional hybrids to reach anthesis and generally reach physiological maturity earlier than conventional cultivars. Semi-dwarf corn plants disclosed herein are less prone to stalk and root lodging due to the shorter stalks and lower ear placement. Corn plants disclosed herein also have the potential to produce high-quality forage due to its high ear-to-stover ratio.

Short stature or semi-dwarf corn plants may also have one or more additional traits, including, but not limited to, increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, increased seed number, increased seed weight, and increased prolificacy, and/or increased harvest index.

According to embodiments of the present disclosure, modified cereal or corn plants are provided that have at least one beneficial agronomic trait and at least one female reproductive organ or ear that is substantially or completely free of off-types. The beneficial agronomic trait may include, but is not limited to, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. As used herein, "harvest index" refers to the mass of the harvested grain divided by the total mass of the above-ground biomass of the plant over a harvested area.

In one aspect, the height at maturity of the corn plant exhibiting semi-dwarf phenotype is reduced by about 10%, 20%, 30%, 40% 60%, or 70% relative to a control plant not provided with the guide RNA and the RNA-guided nuclease grown under comparable conditions.

In another aspect, the yield of the corn plant exhibiting semi-dwarf phenotype is equal to or more then the yield of a control plant not provided with the guide RNA and the RNA-guided nuclease grown under comparable conditions.

In another aspect, the corn plant exhibiting semi-dwarf phenotype requires about 5%, 10%, 15%, 20%, or 25% fewer heat units than a control plant not provided with the guide RNA and the RNA-guided nuclease to reach anthesis.

In yet another aspect, the corn plant exhibiting semi-dwarf phenotype has a relative maturity of about 10%, 15%, 20%, 25%, 30%, 35%, 40%, or 45% fewer days than the relative maturity of a control plant not provided with the guide RNA and the RNA-guided nuclease grown under comparable conditions.

According to one aspect of the present disclosure, a modified corn plant provided herein comprises a height of less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm and an average stem diameter of at least 17.5 mm, at least 18 mm, at least 18.5 mm, at least 19 mm, at least 19.5 mm, at least 20 mm, at least 20.5 mm, at least 21 mm, at least 21.5 mm, or at least 22 mm. According to another aspect the modified corn plant further comprises at least one ear that is substantially free of mature male reproductive tissue.

According to one aspect of the present disclosure a modified corn plant provided herein comprises a height of between 1000 mm and 1600 mm, 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, or between 1000 mm and 1300 mm, and an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. According to another aspect the modified corn plant further comprises at least one ear that is substantially free of mature male reproductive tissue.

According to one aspect of the present disclosure, a modified corn plant provided herein comprises a height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of an unmodified control plant and an stem diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the unmodified control plant. According to another aspect of the present disclosure, a modified corn plant provided herein comprises a height that is between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 75%, between 25% and 75%, between 10% and 50%, or between 50% and 75% less than the height of an unmodified control plant and a stem diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the stem diameter of the unmodified control plant.

According to one aspect of the present disclosure, a modified corn plant provided herein comprises a fresh ear weight that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the fresh ear weight of an unmodified control plant. According to another aspect of the present disclosure, a modified corn plant provided herein comprises a fresh ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the fresh ear weight of an unmodified control plant.

According to one aspect of the present disclosure, a modified corn plant provided herein comprises a harvest index of at least 0.57, at least 0.58, at least 0.59, at least 0.60, at least 0.61, at least 0.62, at least 0.63, at least 0.64, or at least 0.65. According to another aspect of the present disclosure a modified corn plant provided herein comprises a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. According to yet another aspect of the present disclosure, a modified corn plant provided herein comprises a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater as compared to an unmodified control plant. According to still another aspect of the present disclosure, a modified corn plant provided herein comprises a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater as compared to an unmodified control plant.

According to one aspect of the present disclosure, a population of modified corn plants provided herein comprises a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% lower as compared to a population of unmodified control plants. According to another aspect of the present disclosure, a population of modified corn plants provided herein comprises a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% lower as compared to a population of unmodified control plants.

According to one aspect, the present disclosure provides a population of modified corn plants, where the population of modified corn plants shares ancestry with a single modified corn plant, where the population of modified corn plants comprises an average height of 1500 mm or less, wherein the population of modified corn plants comprises an average stem diameter of 18 mm or more, wherein less than 5%, less than 10%, less than 15%, less than 20%, or less than 25% of the population of modified corn plants comprises a height of greater than 1500 mm, and where less than 5%, less than 10%, less than 15%, less than 20%, or less than 25% of the population of modified corn plants comprises at least one ear comprising mature male reproductive tissue. In another aspect the population of modified corn plants comprises an average height of 1200 mm or less.

According to one aspect, the present disclosure provides a population of modified corn plants, where the population of modified corn plants shares ancestry with a single modified corn plant, where the population of modified corn plants comprises an average height of 1500 mm or less, where less than 5%, less than 10%, less than 15%, less than 20%, or less than 25% of the population of modified corn plants comprises a height of greater than 1500 mm, and where the population of modified corn plants comprises a lodging frequency that is at least 5%, at least 10%, at least 20%, at least 30%, at least 40%, at least 50%, at least 60%, at least 70% at least 80%, at least 90%, or 100% lower as compared to a population of unmodified control corn plants.

According to one aspect, the present disclosure provides a modified corn plant comprising a height of 1500 mm or less, where the modified corn plant further comprises a stem diameter of 18 mm or more, and where at least one ear of the modified corn plant is substantially free of mature male reproductive tissue.

According to one aspect, the present disclosure provides a modified corn plant comprising a height of 1500 mm or less, wherein the modified corn plant further comprises a harvest index of at least 0.58, and where the modified corn plant further comprises at least one ear that is substantially free of mature male reproductive tissue.

Exemplary Embodiments

The following are exemplary embodiments of the present specification.

Embodiment 1. A corn plant comprising at least one non-natural brachytic mutation, wherein the corn plant exhibits a semi-dwarf phenotype compared to a control corn plant not comprising the at least one non-natural brachytic mutation when grown under comparable conditions.

Embodiment 2. A brachytic corn plant comprising at least one non-natural brachytic mutation.

Embodiment 3. A brachytic corn plant comprising at least one non-natural brachytic mutant allele.

Embodiment 4. A corn plant comprising at least one non-natural brachytic mutation exhibiting a semi-dwarf phenotype.

Embodiment 5. A corn plant comprising at least one non-natural brachytic mutant allele exhibiting a semi-dwarf phenotype.

Embodiment 6. A modified corn plant comprising a non-naturally occurring mutation in a BR gene reducing the activity of the BR gene, wherein the mutation is not introduced via transposon, and wherein the modified corn plant does not comprise a br2-23 brachytic allele or SNP5259.

Embodiment 7. A modified corn plant comprising a modified BR2 gene with reduced activity, wherein the modified corn plant does not comprise a br2-23 brachytic allele or SNP5259.

Embodiment 8. A non-transgenic corn plant comprising a synthetic mutation in a BR gene reducing the activity of the BR gene.

Embodiment 9. A modified corn plant comprising a non-transgene or non-transposon mediated mutation in a BR gene reducing the activity of the BR gene.

Embodiment 10. A brachytic corn plant comprising a dominant, non-transgenic BR mutant allele.

Embodiment 11. The corn plant of embodiment 1, wherein the BR gene is a BR2 gene.

Embodiment 12. The corn plant of embodiment 1 or 11, wherein the at least one non-natural BR mutation is selected from the group consisting of a substitution, an insertion, an inversion, a deletion, a duplication, and a combination thereof.

Embodiment 13. The corn plant of embodiment 12, wherein the at least one non-natural BR mutation is at least one insertion.

Embodiment 14. The corn plant of embodiment 13, wherein the at least one insertion is within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5' UTR, and a combination thereof.

Embodiment 15. The corn plant of embodiment 14, wherein the at least one insertion is within Exon 5 of the BR2 gene.

Embodiment 16. The corn plant of any one of embodiments 13 to 15, wherein the at least one insertion comprises at least 1 nucleotide, at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

Embodiment 17. The corn plant of embodiment 15, wherein the at least one insertion is a single nucleobase selected from the group consisting of guanine, cytosine, adenine, thymine, or uracil.

Embodiment 18. The corn plant of embodiment 17, wherein the single nucleobase is thymine.

Embodiment 19. The modified corn plant of embodiment 18, wherein the single thymine (T) insertion occurs between nucleotide number 5420 and 5421 according to the BR2 open reading frame.

Embodiment 20. The corn plant of embodiment 12, wherein the at least one non-natural mutation is at least one substitution.

Embodiment 21. The corn plant of embodiment 20, wherein the at least one substitution is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 22. The corn plant of embodiment 12, wherein the at least one non-natural mutation is at least one deletion.

Embodiment 23. The corn plant of embodiment 22, wherein the at least one deletion is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5' UTR, and a combination thereof.

Embodiment 24. The corn plant of embodiment 12, wherein the at least one non-natural mutation is at least one duplication.

Embodiment 25. The corn plant of embodiment 24, wherein the at least one duplication is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 26. The modified corn plant of any one of embodiments 1 to 25 wherein the presence of the non-naturally occurring mutation in the BR gene does not have an adverse impact on the agronomic or quality properties of the corn plant.

Embodiment 27. The modified corn plant of embodiment 26, wherein the height at maturity of the modified corn plant exhibiting semi-dwarf phenotype is reduced by about 10%, 20%, 30%, 40%, 60%, or 70% relative to a control corn plant.

Embodiment 28. The modified corn plant of embodiment 26, wherein the yield of the modified corn plant is equal to or more than the yield of a control corn plant.

Embodiment 29. The modified corn plant of embodiment 26, wherein the corn plant requires about 5%, 10%, 15%, 20%, or 25% fewer heat units than a control plant.

Embodiment 30. The modified corn plant of embodiment 26, wherein the modified corn plant has a relative maturity of about 10%, 15%, 20%, 25%, 30%, 35%, 40%, or 45% fewer days than the relative maturity of a control corn plant.

Embodiment 31. The modified corn plant of any one of embodiments 1 to 30, wherein the at least one non-natural BR mutation is transferred in a dominant fashion.

Embodiment 32. The modified corn plant of embodiment 31, wherein the modified corn plant can generate an antisense BR2 transcript.

Embodiment 33. The corn plant of any one of embodiments 1 to 30, wherein the corn plant is homozygous for the at least one non-natural brachytic mutation.

Embodiment 34. The corn plant of embodiment 33, wherein the at least one non-natural brachytic mutation is selected from the group consisting of a substitution, an insertion, an inversion, a deletion, a duplication, and a combination thereof.

Embodiment 35. The corn plant of embodiment 34, wherein the at least one non-natural brachytic mutation is at least one insertion.

Embodiment 36. The corn plant of embodiment 35, wherein the at least one insertion is within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 37. The corn plant of embodiment 36, wherein the at least one insertion is within Exon 5 of the BR2 gene.

Embodiment 38. The corn plant of embodiment 37, wherein the at least one insertion is a single nucleobase selected from the group consisting of guanine, cytosine, adenine, thymine, or uracil.

Embodiment 39. The corn plant of embodiment 38, wherein the single nucleobase is thymine.

Embodiment 40. The corn plant of embodiment 39, wherein the single thymine (T) insertion occurs between nucleotide number 5420 and 5421 according to the BR2 open reading frame.

Embodiment 41. The corn plant of any one of embodiments 1 to 30, wherein the corn plant is heterozygous for the at least one non-natural brachytic mutation.

Embodiment 42. The corn plant of embodiment 41, wherein the corn plant comprises a wildtype BR2 allele.

Embodiment 43. The corn plant of embodiment 41, wherein the corn plant comprises a native BR2 mutant allele.

Embodiment 44. The corn plant of embodiment 43, wherein the native BR2 mutant allele is br2-MX.

Embodiment 45. The corn plant of embodiment 44, wherein the native BR2 mutant allele comprises an insertion of a transposon of 4.7 kb in Exon 5 of the BR2 gene.

Embodiment 46. The corn plant of any one of embodiments 43 to 45, wherein the corn plant comprises at least one non-natural brachytic mutation selected from the group consisting of a substitution, an insertion, an inversion, a deletion, a duplication, and a combination thereof.

Embodiment 47. The corn plant of embodiment 46, wherein the at least one non-natural brachytic mutation is at least one insertion.

Embodiment 48. The corn plant of embodiment 47, wherein the at least one insertion is within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 49. The corn plant of embodiment 48, wherein the at least one insertion is within Exon 5 of the BR2 gene.

Embodiment 50. The corn plant of embodiment 49, wherein the at least one insertion is a single nucleobase selected from the group consisting of guanine, cytosine, adenine, thymine, or uracil.

Embodiment 51. The corn plant of embodiment 50, wherein the single nucleobase is thymine.

Embodiment 52. The corn plant of embodiment 51, wherein the single thymine (T) insertion occurs between nucleotide number 5420 and 5421 according to the BR2 open reading frame.

Embodiment 53. A method for producing a semi-dwarf corn plant, the method comprising (a) providing a guide RNA that recognizes a target site in a BR gene in a corn cell, wherein the guide RNA acts in association with an RNA-guided nuclease that creates a strand break at the target site, (b) generating a corn plant from the corn cell, and (c) selecting the corn plant exhibiting semi-dwarf phenotype.

Embodiment 54. The method of embodiment 53, further comprising integrating into the strand break a sequence, wherein the strand break is a double-stranded break.

Embodiment 55. The method of embodiment 54, wherein the sequence is a single nucleobase selected from the group consisting of guanine, cytosine, adenine, thymine, or uracil.

Embodiment 56. The method of embodiment 55, wherein the single nucleobase is thymine.

Embodiment 57. The method of embodiment 56, wherein the thymine is inserted between nucleotide number 5420 and 5421 according to the BR2 open reading frame.

Embodiment 58. The method of embodiment 54, wherein the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, or at least 10 nucleotides.

Embodiment 59. The method of any one of embodiments 54, 55, 56, and 58, wherein the sequence is integrated in a BR2 gene.

Embodiment 60. The method of embodiment 59, wherein the sequence is integrated within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 61. The method of embodiment 54, wherein the sequence is introduced by a donor sequence.

Embodiment 62. The method of embodiment 61, wherein the sequence is a single nucleobase selected from the group consisting of guanine, cytosine, adenine, thymine, or uracil.

Embodiment 63. The method of embodiment 62, wherein the single nucleobase is thymine.

Embodiment 64. The method of embodiment 63, wherein the thymine is inserted between nucleotide number 5420 and 5421 according to a BR2 open reading frame.

Embodiment 65. The method of embodiment 61, wherein the sequence comprises at least 2 nucleotides, at least 3 nucleotides, at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, or at least 20 nucleotides.

Embodiment 66. The method of any one of embodiments 61, 62, 63, and 65, wherein the sequence is integrated in a BR2 gene.

Embodiment 67. The method of embodiment 66, wherein the sequence is integrated within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 68. The method of embodiment 53 or 54, further comprising integrating into the strand break at least one substitution, at least one inversion, at least one deletion, at least one duplication, or a combination thereof.

Embodiment 69. The method of embodiment 68, wherein the at least one substitution is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 70. The method of embodiment 68, wherein the at least one deletion is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 71. The method of embodiment 68, wherein the at least one duplication is within a polynucleotide sequence of a BR2 gene selected from the group consisting of a BR2 promoter, Exon 1, Exon 2, Exon 3, Exon 4, Exon 5, Intron 1, Intron 2, Intron 3, Intron 4, 3'UTR, 5' UTR, and a combination thereof.

Embodiment 72. The method of any one of embodiment 53-71, wherein the RNA-guided nuclease is selected from the group consisting of, Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, homologs thereof, or modified versions thereof.

Embodiment 73. The method of embodiment 72, wherein the RNA-guided nuclease is Cas9 comprising a nucleic acid sequence as set forth in SEQ ID NO: 1.

Embodiment 74. The method of embodiment 72 or 73, wherein the RNA-guided nuclease comprises an N terminal nuclear localization sequence, a C terminal nuclear localization sequence, or both.

Embodiment 75. The method of embodiment 73, wherein the Cas9 is encoded by a nucleotide sequence at least 85% identical to SEQ ID NO: 1.

Embodiment 76. The method of embodiment 72, wherein the target site is within a polynucleotide sequence of the BR2 gene selected from the group consisting of a BR2 promoter, Exon 1, Exon 2, Exon 3, Exon 4, Exon 5, Intron 1, Intron 2, Intron 3, Intron 4, 3'UTR, 5'UTR, and a combination thereof.

Embodiment 77. The method of embodiment 76, wherein the target site is within Exon 5.

Embodiment 78. The method of embodiment 77, wherein the target site comprises a nucleotide sequence selected from the group consisting of SEQ ID NOs: 7-17.

Embodiment 79. The method of embodiment 77, wherein the target site comprises a sequence as set forth in SEQ ID NO: 15.

Embodiment 80. The method of embodiment 79, wherein the guide RNA comprises a sequence as set forth in SEQ ID NO: 6.

Embodiment 81. The method of embodiment 53 to 80, wherein the plant exhibiting semi-dwarf phenotype is homozygous, hemizygous, or heterozygous for the BR gene.

Embodiment 82. The method of embodiment 81, wherein the plant exhibiting semi-dwarf phenotype is homozygous for the BR gene.

Embodiment 83. The method of embodiment 82, wherein the plant exhibiting semi-dwarf phenotype comprises at least one non-natural brachytic mutation selected from the group consisting of a substitution, an insertion, an inversion, a deletion, a duplication, and a combination thereof.

Embodiment 84. The method of embodiment 83, wherein the at least one non-natural brachytic mutation is at least one insertion.

Embodiment 85. The method of embodiment 84, wherein the at least one insertion is within Exon 5 of the BR2 gene.

Embodiment 86. The method of embodiment 85, wherein the at least one insertion is a single thymine (T) insertion that occurs between nucleotide number 5420 and 5421 according to the BR2 open reading frame.

Embodiment 87. The method of embodiment 81, wherein the plant exhibiting semi-dwarf phenotype is heterozygous for the BR gene.

Embodiment 88. The method of embodiment 87, wherein the plant exhibiting semi-dwarf phenotype comprises a wildtype BR2 allele.

Embodiment 89. The method of embodiment 87, wherein the plant exhibiting semi-dwarf phenotype comprises a native BR2 mutant allele.

Embodiment 90. The method of embodiment 89, wherein the native BR2 mutant allele is br2-MX.

Embodiment 91. The method of embodiment 89, wherein the native BR2 mutant allele comprises an insertion of a transposon of 4.7 kb in Exon 5 of the BR2 gene.

Embodiment 92. The method of any one of embodiments 89 to 91, wherein the plant exhibiting semi-dwarf phenotype comprises at least one non-natural brachytic mutation selected from the group consisting of a substitution, an insertion, an inversion, a deletion, a duplication, and a combination thereof.

Embodiment 93. The method of embodiment 92, wherein the at least one non-natural brachytic mutation is at least one insertion.

Embodiment 94. The method of embodiment 93, wherein the at least one insertion is within Exon 5 of the BR2 gene.

Embodiment 95. The method of embodiment 94, wherein the at least one insertion is a single thymine (T) insertion that occurs between nucleotide number 5420 and 5421 according to the BR2 open reading frame.

Embodiment 96. The method of embodiment 53, wherein the height at maturity of the corn plant exhibiting semi-dwarf phenotype is reduced by about 10%, 20%, 30%, 40%, 60%, or 70% relative to a control plant not provided with the guide RNA and the RNA-guided nuclease grown under comparable conditions.

Embodiment 97. The method of embodiment 53, wherein the yield of the corn plant exhibiting semi-dwarf phenotype is equal to or more then the yield of a control plant not provided with the guide RNA and the RNA-guided nuclease grown under comparable conditions.

Embodiment 98. The method of embodiment 53, wherein the corn plant exhibiting semi-dwarf phenotype requires about 5%, 10%, 15%, 20%, or 25% fewer heat units than a control plant not provided with the guide RNA and the RNA-guided nuclease to reach anthesis.

Embodiment 99. The method of embodiment 53, wherein the corn plant exhibiting semi-dwarf phenotype has a relative maturity of about 10%, 15%, 20%, 25%, 30%, 35%, 40%, or 45% fewer days than the relative maturity of a control plant not provided with the guide RNA and the RNA-guided nuclease grown under comparable conditions.

Embodiment 100. A CRISPR based genome editing system comprising Cas9 and a guide RNA, wherein the CRISPR based genome editing system reduces the activity of a BR gene.

Embodiment 101. The CRISPR based genome editing system of embodiment 100, wherein the BR gene is a BR2 gene.

Embodiment 102. The CRISPR based genome editing system of embodiment 101, wherein the Cas9 is encoded by a nucleotide sequence as set forth in SEQ ID NO: 1.

Embodiment 103. The CRISPR based genome editing system of embodiment 100, wherein the Cas9 is encoded by a nucleotide sequence at least 85% identical to SEQ ID NO: 1.

Embodiment 104. The CRISPR based genome editing system of embodiment 101, wherein the guide RNA comprises a sequence as set forth in SEQ ID NO: 6.

Embodiment 105. A method of cleaving a BR gene in a corn cell, comprising providing a guide RNA and an RNA-guided nuclease into the corn cell, wherein the guide RNA acts in association with the RNA-guided nuclease to create a strand break at a target site.

Embodiment 106. The method of embodiment 105, further comprising integrating into the strand break a nucleic acid sequence.

Embodiment 107. The method of embodiment 106, wherein the RNA-guided nuclease is Cas9.

Embodiment 108. The method of embodiment 105, wherein the BR gene is a BR2 gene.

Embodiment 109. The method of embodiment 105, wherein the target site comprises a sequence selected from the group consisting of SEQ ID NOs: 7-17.

Embodiment 110. The method of embodiment 105, wherein the guide RNA comprises a sequence as set forth in SEQ ID NO: 6.

Embodiment 111. The method of embodiment 105, wherein the RNA-guided nuclease comprises a sequence as set forth in SEQ ID NO: 2.

Embodiment 112. The method of any one of embodiments 105 to 111, wherein the corn cell expresses a truncated BR protein that results in a semi-dwarf phenotype.

EXAMPLES

Example 1

Generate a Corn Plant Exhibiting Semi-Dwarf Phenotype
Creation of a Construct Expressing a Recombinant Cas9

A corn optimized version of the *Streptococcus thermophilus* LMD9 Cas9 is cloned into a vector together with N and C terminal nuclear localization signal (NLS) and an internal intron ("recombinant Cas9"). The nucleotide sequence of the recombinant Cas9 is as set forth in SEQ ID NO: 1, and its amino acid sequence is as set forth in SEQ ID NO: 2. The N and C terminal NLSs are located at nucleotide positions 4-33, and 3586-3615 of SEQ ID NO: 1, respectively, and the internal intron is located at nucleotide position 507-695 of SEQ ID NO: 1. The recombinant Cas9 protein is expressed under the Dahlia Mosaic Virus (DaMV) promoter (SEQ ID NO: 3). The recombinant Cas9 protein is capable of binding to a Protospacer Adjacent Motif (PAM) having a DNA sequence of 5'AGAA'3. The AGAA PAM sequence serves as a binding signal for Cas9 and the presence of this sequence is required for DNA cleavage mediated by the recombinant Cas9.

Search for the BR2 Gene Target Sites

The corn BR2 gene sequence is searched for potential AGAA PAM sequences with a configuration of N-20-NNA-GAA. This sequence serves as the binding site for the recombinant Cas9. Consequently, 11 target guide RNA (gRNA) sequences adjacent to an AGAA PAM sequence are selected as shown in the table below:

TABLE 1

Target sequence of the BR2 gene

| gRNA | SEQ ID NO | Target gRNA Sequence | SEQ ID NO (sgRNA) |
|---|---|---|---|
| Br2gRNA1 | 7 | TACAGTCCGCCGATCATGAC | 34 |
| Br2gRNA2 | 8 | TGGGCGGCTGCTCGGTCTCC | 35 |
| Br2gRNA3 | 9 | TCCGCCGGCGCCAATGACAG | 36 |
| Br2gRNA4 | 10 | GAGGCCCGCACGTCGGTGTC | 37 |
| Br2gRNA5 | 11 | TTCCCGGCGGGCACGCTCAG | 38 |
| Br2gRNA6 | 12 | ATCGCCTGGTTCGACGCGGA | 39 |
| Br2gRNA7 | 13 | GACCGCATCTCCGTCATCGT | 40 |
| Br2gRNA8 | 14 | GTCGTGGGCGCCACCGTGCT | 41 |
| Br2gRNA9 | 15 | TGCGCGGCCTCCAGGTCCCC | 6 |

TABLE 1-continued

Target sequence of the BR2 gene

| gRNA | SEQ ID NO | Target gRNA Sequence | SEQ ID NO (sgRNA) |
|---|---|---|---|
| Br2gRNAo1 | 16 | ATGTCCGGCCGCGACGGGTA | 42 |
| Br2gRNAo2 | 17 | CTGTTCGCGACGAGCATCAG | 43 |

The target sequence of each of the above BR2gRNAs is operably linked to a promoter sequence (SEQ ID NO: 4) at its 5' end and a scaffold guide gRNA sequence at its 3' end (SEQ ID NO: 5). The resulting complete single guide RNA (sgRNA) sequences are as set forth in the right most column of Table I.

One of the target gRNA sequences above, Br2gRNA9 as set forth in SEQ ID NO: 15, is operably linked to a promoter sequence (SEQ ID NO: 4) at its 5' end and a scaffold guide gRNA sequence at its 3' end (SEQ ID NO: 5). The resulting sequence (SEQ ID NO: 6) is expressed via a vector in corn cells as described below.

Additional gRNA sequences for the BR2 gene are as set forth in SEQ ID NOs: 24-26. Complete sequences including a promoter (SEQ ID NO: 4) at the 5' end of each of SEQ ID NO: 24-26 are as set forth in SEQ ID NO: 31-33, respectively. Sequences set forth in SEQ ID NOs: 20-23 are gRNA sequences capable of binding to a corn optimized version of the *Streptococcus pyogenes* Cas9 and targeting the BR2 gene for genome editing. Expression cassette sequences including a promoter (SEQ ID NO: 4) at the 5' end of each of SEQ ID NO: 20-23 are set forth in SEQ ID NOs: 27-30, respectively.

Testing of Insertion of Blunt-End Double Strand DNA Fragment

Functional gRNAs for the CRISPR/Cas9 system are evaluated for their targeting efficacy in inserting a blunt-end double-stranded DNA (dsDNA) into the cut site of the BR2 gene. If the recombinant Cas9 possesses an endonuclease activity and introduces a double strand break (DSB) in the protospacer of the selected BR2 target site, the endogenous corn non-homologous end-joining (NHEJ) DNA repair system will insert the blunt-end dsDNA into the DSB.

The 11 sgRNAs of Table I are selected and expressed in a vector using the promoter as set forth in SEQ ID NO: 4 as described above. Protoplasts testing of the Cas9/gRNA efficacy are conducted as follows: corn leaf protoplasts are transformed with (1) 0.8 pmol of a plasmid expressing the recombinant Cas9 protein, (2) 1.6 pmol gRNA plasmid, and (3) 50 pmol of pre-annealed blunt-end dsDNA (SEQ ID NOs: 18 and 19). To test for transformation efficiency, 2.5 µg of a construct encoding green fluorescent protein (GFP) is also included in the protoplast transformation. A standard PEG-mediated protocol is used to transform aliquots of corn leaf protoplast suspensions containing about 320,000 cells.

Two days later, an aliquot of the transformed corn leaf protoplasts is collected to calculate transfection frequency on the PE Operetta® Imaging System (PerkinElmer, Waltham, MA) which calculates the ratio of GFP positive cells per total cells. Omission of the recombinant Cas9 expression cassette during the corn protoplast transformation served as a negative control. Protoplasts are harvested 48 hours post transfection and analyzed for insertion of the blunt-end double-strand DNA fragment into the target sites by using PCR with an oligo specific primer and a gene specific primer.

Two target sequences are identified to be capable of inserting the blunt-end dsDNA into the corresponding target sites of the BR2 gene. The target sequence (SEQ ID NO: 15) with the least potential off-targets is chosen for stable transformation (complete sequence for expression is as set forth in SEQ ID NO: 6).

Transformation and Regeneration of Corn Plants

Standard *Agrobacterium tumefaciens*-mediated transformation is used to transform a 01DKD2 corn plants with Cas9 and gRNA using a transfer DNA (T-DNA) binary vector system. Briefly, a binary vector is created containing the glyphosate resistance CP4 marker and sequences encoding the recombinant Cas9 and the gRNA (SEQ ID NO: 6) under the control of the 35 S cauliflower mosaic virus (CaMV) promoter. A standard helper vector is created. Both vectors are immobilized into competent *Agrobacterium tumefaciens* strains. By way of non-homologous end joining (NHEJ), a single nucleobase thymine (T) is added in Exon 5 of the BR2 gene between nucleotide number 5420 and 5421 according to the BR2 open reading frame (ORF), or between nucleotide number 2907 and 2908 of the ORF after the removal of introns, and thus creating a premature stop codon therein, which leads to a truncated BR2 protein.

Shoot-tips from the transformed 01DKD2 corn plants inoculated with the *Agrobacterium turnefaciens* strains are selected for transgenic plants by using glyphosate containing medium. The regenerated plantlets are subsequently transferred to vessels and planted into soil in the growth room.

Selection of Semi-Dwarf Corn Plants

The semi-dwarf trait associated with the BR2 gene in corn is transferred via a recessive allele. The selection of transgenic corn plants with a semi-dwarf trait is performed by growing and selfing the first backcross generation to determine which plants carry the recessive alleles. Additional progeny testing in successive backcross generations are conducted to determine the presence of the locus of interest. The last backcross generation is usually selfed to give pure breeding progeny for the truncated BR2 genes.

Figure 2:
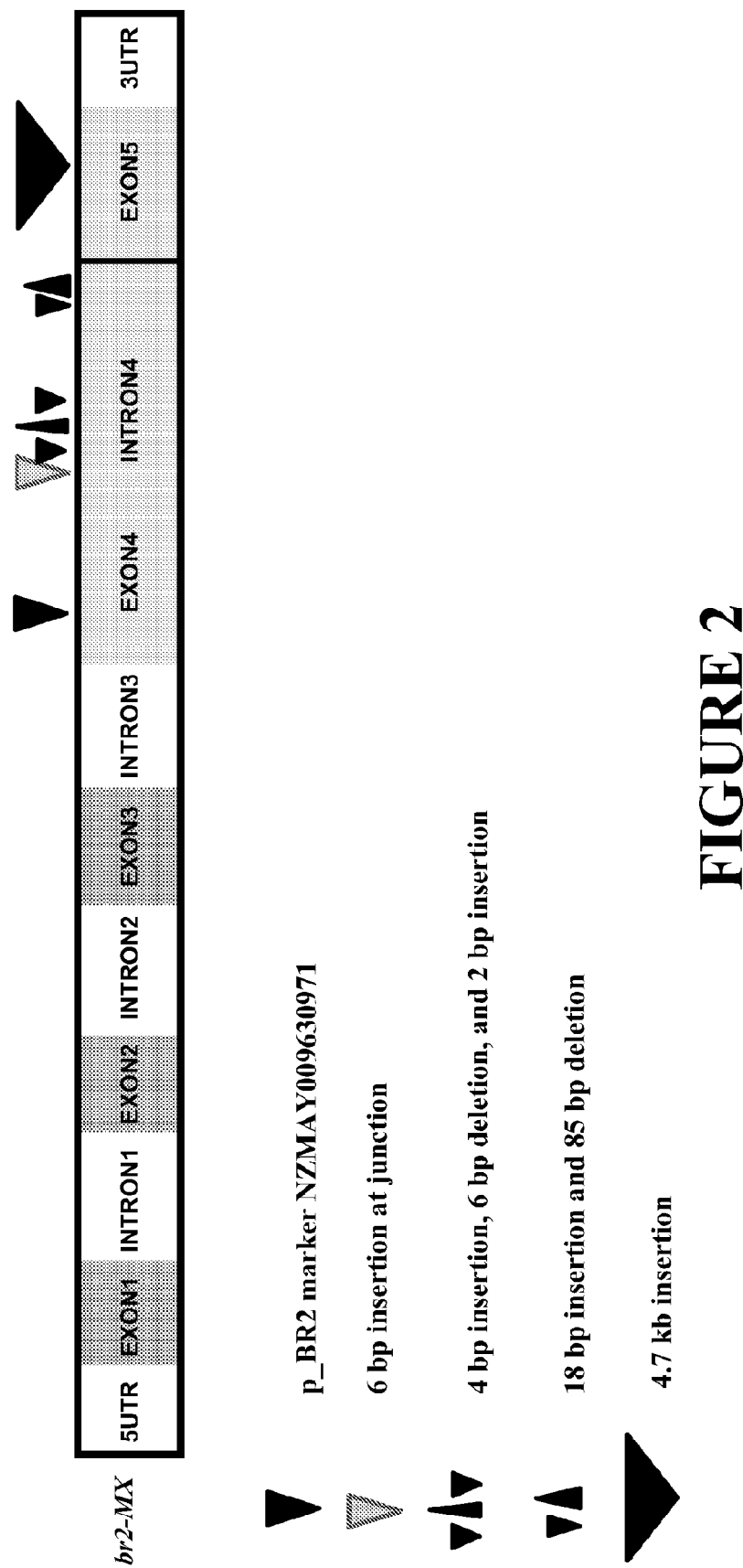
FIG. 2 schematically illustrates the structure of a native BR2 mutant allele, br2-MX, and its polymorphisms and mutations.

A native BR2 mutant exhibiting a semi-dwarf phenotype is used as a control. The native BR2 mutant comprises a br2-MX allele. As shown in FIG. 2, Intron 4 contains multiple insertions and deletions. A 4.7 kb insertion in Exon 5 introduces a premature stop codon therein.

Semi-Dwarf Phenotype

Genome edited corn plants exhibiting a semi-dwarf phenotype is as shown in FIGS. 3-6.

Figure 3:
FIG. 3 shows reduced plant height (semi-dwarf) of a genome edited RI corn plant at V6 growth stage expressing a truncated BR2 protein due to a single T insertion in Exon 5, in comparison to a wild-type control plants.

FIG. 3 shows reduced plant height (semi-dwarf) of a genome edited R1 corn plant at V6 growth stage expressing a truncated BR2 protein due to the single T insertion in Exon 5, in comparison to a wild-type control plants.

Figure 4:
FIG. 4 shows reduced plant height (semi-dwarf) of a genome edited BR2 01DKD2 corn plant expressing a truncated BR2 protein due to a single T insertion in Exon 5, in comparison to wild-type control.

FIG. 4 shows reduced plant height (semi-dwarf) of a genome edited BR2 OIDKD2 corn plant expressing a truncated BR2 protein due to the single T insertion in Exon 5, in comparison to wild-type control.

Figure 5A:
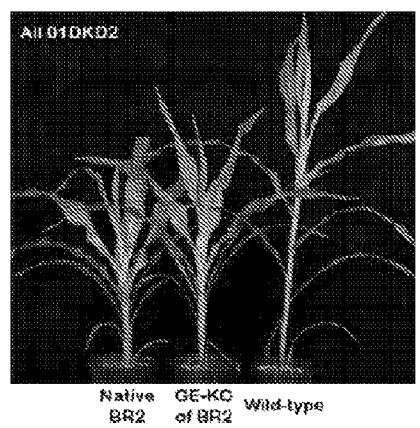
FIG. 5A shows reduced plant height (semi-dwarf) of a genome edited BR2 corn plant expressing a truncated BR2 protein due to a single T insertion in Exon 5 ("br2-GE" hereinafter), in comparison to a native br2-MX mutant and a wild-type control.

FIG. 5A shows reduced plant height (semi-dwarf) of a genome edited BR2 corn plant expressing a truncated BR2 protein due to the single T insertion in Exon 5, in comparison to the native br2-MX mutant and a wild-type control. The reduction in plant height of the genome edited plant is similar to that of the native br2-MX mutant plant. Both plants show a significant reduction in height compared to the wild-type control.

Figure 5B:
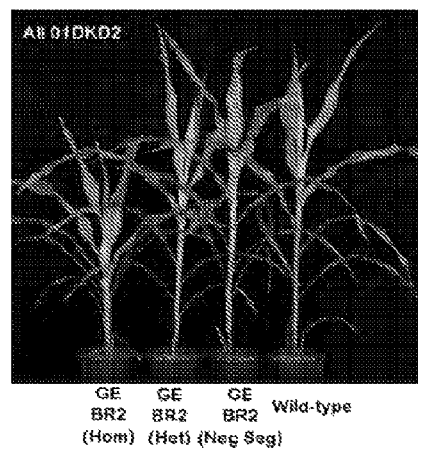
FIG. 5B shows reduced plant height of a homozygous genome edited BR2 plant expressing a truncated BR2 protein due to a single T insertion in Exon 5, in comparison to a heterozygous genome edited BR2 plant, a negative segregation genome edited BR2 plant, and a wild-type control.

FIG. 5B shows reduced plant height of a homozygous genome edited BR2 plant expressing a truncated BR2 protein due to the single T insertion in Exon 5, in comparison to a heterozygous genome edited BR2 plant, a negative segregation genome edited BR2 plant, and a wild-type control. Only the homozygous genome edited BR2 plant exhibits the semi-dwarf phenotype, indicating this trait is transmitted in a recessive fashion.

Figure 6:
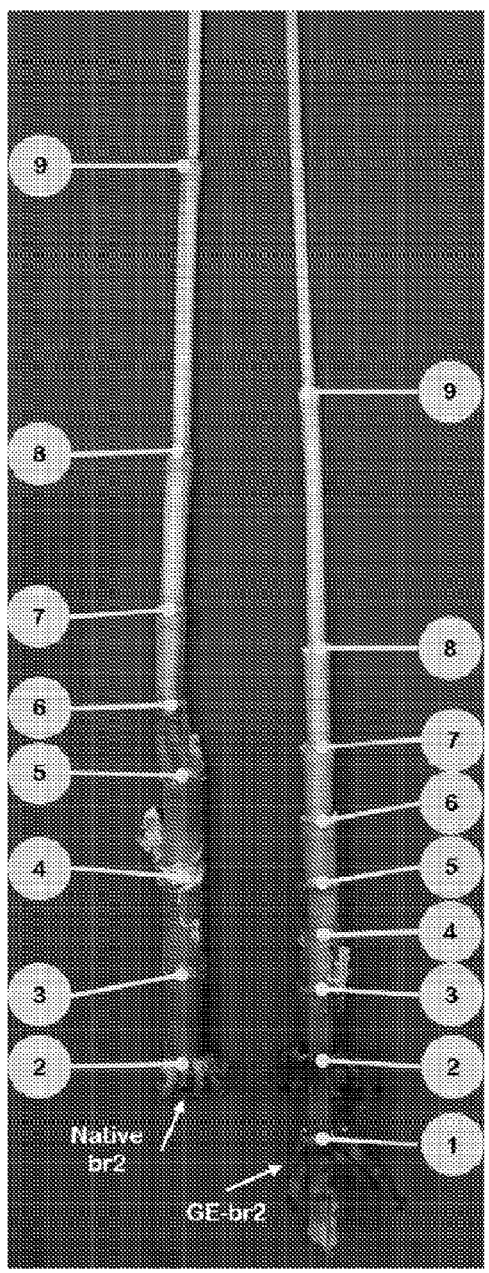
FIG. 6 shows shorter internodes of a genome edited BR2 corn plant expressing a truncated BR2 protein due to the single T insertion in Exon 5, in comparison to a native BR2 wild-type control.

FIG. 6 shows shorter internodes of a genome edited BR2 corn plant expressing a truncated BR2 protein due to the single T insertion in Exon 5, in comparison to a native BR2 wild-type control.

Example 2

Introgression of a BR2 Brachytic Allele to Produce a new Brachytic Variety

A corn plant comprising a brachytic allele disclosed herein is crossed with another non-brachytic corn line comprising a desirable trait (e.g., improved yield under drought, cold, heat stress conditions). $F_1$ progeny plants from this cross is assayed for the single thymine (T) insertion in Exon 5 of the BR2 gene between nucleotide number 5420 and 5421 according to the ORF of the BR2 gene. A selected $F_1$ progeny plant is then backcrossed with the parent non-brachytic corn line comprising the desirable trait (recurrent parent). Plants from the BC1 generation are also genotyped for the single T insertion to select for the brachytic allele. After multiple rounds of backcrossing (e.g., 5-7 generations), a new brachytic corn line is obtained comprising the desirable trait in the recurrent parent elite line.

Example 3

Generation of br2 Hybrid Corn Plants

Through breeding, br2 hybrid corn plants are generated by crossing a non-br2/wildtype or a br2 native mutant (br2-MX) with a br2 genome edited mutant (br2-GE). The hybrid corn plants that are grown and measured in field experiments disclosed herein are summarized in Table 2 below:

TABLE 2 br2 hybrid and control corn plants

| br2 hybrids (named by two parent inbreds flanking "+") | Genotype at the BR2 locus |
| --- | --- |
| 01DKD2-ZAB-R1 + CV666824 | br2-GE/br2-MX |
| CV648265 + CV666824 | br2-MX/br2-MX |
| 01DKD2-ZAB-R1 + CV126318 | br2-GE/WT |
| 01DKD2 + CV126318 | WT/WT |
| CV648265 + CV126318 | br2-MX/WT |
| 01DKD2 + CV666824 | WT/br2-MX |

Of note, 01DKD2-ZAB-R1 denotes genome edited br2 with a single T insertion in Exon 5 of the BR2 gene between nucleotide number 5420 and 5421 of the BR2 ORF in maize (br2-GE). CV666824 and CV648265 denote the same native br2 mutant from Mexico in which a 4.7 kb transposon is inserted in Exon 5 of the BR2 gene (br2-MX), causing a premature stop codon resulting in a putative truncated BR2 protein of 1234 amino acid residues. 01DKD2 and CV126318 are both non-brachytic (wildtype) inbred corn plants.

Example 4

Phenotype of br2 Hybrid Corn Plants—Field Experiments br2 hybrid corn plants are planted in a field under natural disease conditions with standard agronomic practices. Specifically, eight rows of corn plants are planted (30 inches between two rows) with 12 corn plants per row. Plant height is measured up to the upper ligule leaf at the R3 stage ("PHTR3") and ear height is measured up to ear node at the R3 stage ("EHTR3"). Stalk diameter is measured at two leaves below the ear at the R3 stage ("STDIEM2R3").

Other traits related to flowering or yield component are also measured as follows: the time in days between pollen shed and silk emergence (anthesis-silking interval or "ASI"); the time in days to 50% pollen shedding at the R1 stage ("P50DR1"); the time in days to 50% visible silk at the R1 stage ("S50DR1"); ear diameter measured by imaging at the R6 stage ("EDR6"); ear area (one side measured by imaging) at the R6 stage ("EAIMAR6"); ear automation volume at the R6 stage ("EAVR6"); ear calculated volume at the R6 stage ("ECVR6"); ear void percentage at the R6 stage ("EVPCTR6"); ear tip void at the R6 stage ("ETVR6"); ear tip void percentage ("ETVPCR6"); ear length measured by imaging at the R6 stage ("ELENR6"); single kernel weight at the R6 stage ("SKWTR6"); kernels per unit area at the R6 stage ("KARR6"); and ear void measured by imaging at the R6 stage ("EVR6").

TABLE 3

Plant height reduction in 01DKD2-ZAB-R1 + CV666824

| Trait | No. of rows | 01DKD2-ZAB-R1 + CV666824 (mean) | CV648265 + CV666824 (mean) | Mean difference | p-value |
| --- | --- | --- | --- | --- | --- |
| Plant height traits | | | | | |
| EHTR3 | 8 | 21.9 | 26.7 | 4.8 | 0.00 |
| PHTR3 | 8 | 48 | 54.2 | 6.2 | 0.00 |
| Flowering or yield component traits | | | | | |
| ASI | 8 | 36.6 | 30.5 | −6.1 | 0.48 |
| P50DR1 | 8 | 57.5 | 57.6 | 0.1 | 0.66 |
| S50DR1 | 8 | 58.5 | 58.6 | 0.1 | 0.69 |
| EDR6 | 14 | 1.9 | 1.8 | −0.1 | 0.67 |
| EAIMAR6 | 14 | 11.2 | 11.0 | −0.2 | 0.60 |
| EAVR6 | 14 | 14.7 | 14.4 | −0.3 | 0.55 |
| ECVR6 | 14 | 19.4 | 19.1 | −0.3 | 0.63 |

As shown in Table 3 above, 01DKD2-ZAB-R1+ CV666824 (comprising one br2-GE allele and one br2-MX native mutant allele) has an average ear height reduction (EHTR3) of 4.8 inches and an average plant height reduction (PHTR3) of 6.2 inches, compared to CV648265+CV666824 (comprising two of br2-MX native mutant alleles). Both the ear height reduction and the plant height reduction are statistically significant with p-value<0.01.

On the other hand, no statistically significant differences are observed for flowering or yield component traits, including ASI, P50DR1, S50DR1, EDR6, EAIMAR6, EAVR6, and ECVR6.

TABLE 4

Plant height reduction and stalk diameter increase in 01DKD2-ZAB-R1 + CV666824

| Trait | No. of rows | 01DKD2-ZAB-R1 + CV666824 (mean) | 01DKD2 + CV666824 (mean) | Mean difference | p-value |
| --- | --- | --- | --- | --- | --- |
| Plant height/diameter traits | | | | | |
| EHTR3 | 6 | 21.9 | 45.9 | 24.0 | 0.00 |
| PHTR3 | 6 | 48.0 | 82.6 | 34.6 | 0.00 |
| STDIEM2R3 | 6 | 1.3 | 1.0 | −0.3 | 0.00 |

TABLE 4-continued

Plant height reduction and stalk diameter increase in 01DKD2-ZAB-R1 + CV666824

| Trait | No. of rows | 01DKD2-ZAB-R1 + CV666824 (mean) | 01DKD2 + CV666824 (mean) | Mean difference | p-value |
|---|---|---|---|---|---|
| Flowering or yield component traits | | | | | |
| EDR6 | 10 | 1.9 | 1.8 | −0.1 | 0.56 |
| EVPCTR6 | 10 | 40.3 | 38.6 | −1.7 | 0.35 |
| EAIMAR6 | 10 | 11.2 | 10.7 | −0.5 | 0.14 |
| ETVR6 | 10 | 1.5 | 1.5 | 0.0 | 0.17 |
| ETVPCR6 | 10 | 51.9 | 51.8 | −0.1 | 0.99 |
| EAVR6 | 10 | 14.7 | 14.0 | −0.7 | 0.16 |
| ELENR6 | 10 | 7.2 | 6.9 | −0.3 | 0.13 |
| EVR6 | 10 | 4.4 | 4.1 | −0.3 | 0.07 |
| ECVR6 | 10 | 19.4 | 18.7 | −0.7 | 0.27 |

As shown in Table 4 above, 01DKD2-ZAB-R1+CV666824 (comprising one br2-GE allele and one br2-MX native mutant allele) has an average ear height reduction (EHTR3) of 24 inches and an average plant height reduction (PHTR3) of 34.6 inches, compared to 01DKD2+CV666824 (comprising a wildtype allele and one br2-MX native mutant allele). Further, 01DKD2-ZAB-R1+CV666824 has an average of 0.3 inches of increase in stalk diameter (STDIEM2R3) compared to 01DKD2+CV666824. All these three measurements are statistically significant with p-value <0.01.

On the other hand, no statistically significant differences are observed for flowering or yield component traits, including EDR6, EVPCTR6, EAIMAR6, ETVR6, ETVPCR6, EAVR6, ELENR6, EVR6, and ECVR6.

TABLE 5

Plant height reduction in 01DKD2-ZAB-R1 + CV126318

| Trait | No. of rows | 01DKD2-ZAB-R1 + CV126318 (mean) | 01DKD2 + CV126318 (mean) | Mean difference | p-value |
|---|---|---|---|---|---|
| Plant height traits | | | | | |
| EHTR3 | 8 | 43.6 | 45.6 | 2.0 | 0.04 |
| PHTR3 | 8 | 83.5 | 85.7 | 2.2 | 0.02 |
| Flowering or yield component traits | | | | | |
| ASI | 8 | 11.3 | 18.9 | 7.6 | 0.32 |
| P50DR1 | 8 | 59.3 | 59.0 | −0.3 | 0.43 |
| S50DR1 | 8 | 59.6 | 59.6 | 0.0 | 0.99 |
| KPER6 | 9 | 473.4 | 468.0 | −5.4 | 0.83 |
| ETVPCR6 | 12 | 48.5 | 49.3 | 0.8 | 0.71 |
| EAVR6 | 12 | 14.4 | 14.8 | 0.4 | 0.52 |
| ELENR6 | 12 | 6.8 | 6.9 | 0.1 | 0.31 |
| EDR6 | 12 | 1.9 | 1.9 | 0.0 | 0.88 |
| EAIMAR6 | 12 | 10.7 | 11.0 | 0.3 | 0.40 |
| SKWTR6 | 9 | 0.0 | 0.0 | 0.0 | 0.68 |
| ETVR6 | 12 | 1.4 | 1.4 | 0.0 | 0.32 |
| ECVR6 | 12 | 19.3 | 19.7 | 0.4 | 0.61 |
| KARR6 | 9 | 337.5 | 312.4 | −25.1 | 0.34 |
| EVPCTR6 | 12 | 38.3 | 38.2 | −0.1 | 0.97 |
| EVR6 | 12 | 4.0 | 4.1 | 0.1 | 0.50 |

As shown in Table 5 above, 01DKD2-ZAB-R1+CV126318 (comprising one br2-GE allele and one wildtype BR2 allele) has an average ear height reduction (EHTR3) of 2.0 inches and an average plant height reduction (PHTR3) of 2.2 inches, compared to 01DKD2+CV126318 (comprising two wildtype BR2 alleles). These measurements are statistically significant with p-value <0.04.

On the other hand, no statistically significant differences are observed for flowering or yield component traits, including ASI, P50DR1, S50DR1, KPER6, ETVPCR6, EAVR6, ELENR6, EDR6, EAIMAR6, SKWTR6, ETVR6, ECVR6, KARR6, EVPCTR6, and EVR6.

What is claimed is:

1. A method for producing a semi-dwarf corn plant with reduced ear height and increased stalk diameter, the method comprising:
   a. providing to a corn cell a guide RNA that recognizes a target site in a BR2 gene in the corn cell, wherein the guide RNA comprises a target site sequence operably linked to a scaffold sequence comprising SEQ ID NO: 5, wherein the guide RNA acts in association with a CRISPR-based RNA-guided nuclease that creates a strand break at the target site which results in an edited br2 mutant allele, wherein the CRISPR-based RNA-guided nuclease is capable of binding to a protospacer adjacent motif (PAM) for Cas9 or Cpf1, and wherein the target site sequence is selected from the group consisting of SEQ ID NOs: 7-17;
   b. generating a corn plant from the corn cell; and
   c. selecting the corn plant exhibiting semi-dwarf phenotype, reduced ear height, and increased stalk diameter relative to a non-edited control corn plant.

2. The method of claim 1, further comprising integrating into the strand break a sequence, wherein the strand break is a double-stranded break.

3. The method of claim 2, wherein the sequence is a single thymine nucleobase inserted between nucleotide number 5420 and 5421 according to the BR2 open reading frame.

4. The method of claim 1, wherein the guide RNA comprises a sequence at least 95% identical to SEQ ID NO: 6.

5. The method of claim 1, wherein the corn plant exhibiting semi-dwarf phenotype, reduced ear height, and increased stalk diameter is heterozygous for the edited br2 mutant allele.

6. The method of claim 5, wherein the corn plant exhibiting semi-dwarf phenotype, reduced ear height, and increased stalk diameter comprises a native BR2 mutant allele.

7. The method of claim 6, wherein the native BR2 mutant allele is br2-MX.

8. The method of claim 1, wherein said target site is in a BR2 gene region selected from the group consisting of Exon 1, Exon 2, Exon 3, Exon 4, Exon 5, 3'UTR, 5'UTR, Intron 1, Intron 2, Intron 3, and Intron 4.

9. The method of claim 1, wherein said CRISPR based RNA-guided nuclease is Cas9.

10. The method of claim 1, wherein said CRISPR based RNA-guided nuclease is Cpf1.

11. The method of claim 1, wherein the corn plant exhibiting semi-dwarf phenotype, reduced ear height, and increased stalk diameter comprises one or more insertions, deletions, substitutions, or inversions in said BR2 gene.

12. The method of claim 1, wherein the PAM has the DNA sequence of NGG, NAG, or AGAA.

13. The method of claim 1, wherein the corn plant exhibiting semi-dwarf phenotype, reduced ear height, and increased stalk diameter is homozygous for the edited br2 mutant allele.

14. The method of claim 1, wherein the guide RNA further comprises the target site sequence operably linked to a promoter sequence comprising SEQ ID NO: 4.

* * * * *

SEQUENCE LISTING

<160> NUMBER OF SEQ ID NOS: 43

<210> SEQ ID NO 1
<211> LENGTH: 3618
<212> TYPE: DNA
<213> ORGANISM: Artificial Sequence
<220> FEATURE:
<223> OTHER INFORMATION: Synthetic Sequence

<400> SEQUENCE: 1

```
atgggatcta agaagagaag aattaaacaa gatatgagtg acctggtgct agggttggat      60
ataggcattg gctccgtggg ggttggcatt cttaataagg tgaccggcga aataattcat     120
aaaaactcac gcatctttcc agcagcccag gctgagaaca atctggtccg tagaaccaac     180
cggcagggtc gaaggttagc caggcgcaag aagcacagac gggtccggct caacaggctt     240
ttcgaggagt ctggtttgat caccgatttc actaagattt ctatcaacct gaatccttat     300
cagctgcgcg ttaaaggtct cacagacgaa cttagcaacg aagagttgtt catcgccctg     360
aaaaatatgg tcaagcatcg cggcattagc tacctggacg acgcttcgga tgatggcaac     420
agtagtgtag gtgactacgc tcagatcgtg aaagagaact cgaagcaatt ggagaccaag     480
accccgggcc aaattcaact cgaaaggtaa gtttctgctt ctacctttga tatatatata     540
ataattatca ttaattagta gtaatataat atttcaaata ttttttttcaa aataaaagaa     600
```

```
tgtagtatat agcaattgct tttctgtagt ttataagtgt gtatatttta atttataact    660
tttctaatat atgaccaaaa tttgttgatg tgcaggtacc agacgtatgg acagttacga    720
ggcgatttta ccgttgaaaa ggatggtaag aagcacaggc tgattaatgt gtttccgacc    780
tcagcttatc gctctgaggc gctgcgtatt ttgcagaccc aacaggaatt taacccgcaa    840
ataacggacg agttcataaa ccgatactta gagattctta caggtaaacg taaatactat    900
cacggcccag gaaatgaaaa gtccaggaca gattatggtc gatatcgcac ttccggagag    960
actctcgaca atatctttgg cattcttata ggcaaatgta ccttctaccc tgacgaattt   1020
agagcagcga aggcttcata tacagcacaa gagtttaatc ttctcaacga cctcaacaac   1080
ttgactgtgc ctactgaaac caaaaagctt agcaaggagc aaaaaaatca aatcattaac   1140
tatgttaaga atgagaaagc tatggggccc gcaaaattgt tcaagtacat agctaagtta   1200
cttagctgtg acgttgctga tattaagggt taccgtattg acaagtctgg taaagctgaa   1260
attcacacct ttgaggctta taggaagatg aagacccttg agacacttga cattgagcag   1320
atggataggg agactttgga caaactggca tacgtcttga cattgaacac cgaaagggaa   1380
ggcatccagg aagctctgga acatgaattt gcagatggtt cgttcagcca aaaacaggtt   1440
gacgagctgg tccaatttag aaaggcaaac tcaagcatat tcggtaaagg ttggcacaac   1500
ttcagcgtta agctgatgat ggaactcatt ccagaattat atgaaacctc tgaggaacag   1560
atgacgattc tcacaagatt gggtaagcag aaaacaacca gctctagcaa taagactaaa   1620
tacattgacg aaaagctcct caccgaagag atttataacc cggtcgtggc aaagagtgta   1680
cggcaagcca tcaagatcgt taatgccgct atcaaggagt atggtgattt tgataatatt   1740
gtgattgaaa tggcacgcga gactaacgag gacgacgaga agaaagctat acagaagatt   1800
caaaaggcta ataaggacga gaaggacgcc gcaatgctaa aggcggccaa tcaatataat   1860
gggaaggctg aactacctca tagcgtcttc catggacata agcaattagc aactaaaata   1920
agattatggc accagcaagg cgaacggtgt ctttatacag gtaaaacgat atctattcac   1980
gacctgatta acaactctaa ccagtttgaa gtggatcata tcttaccact aagtatcacc   2040
ttcgacgatt cacttgctaa caaggtgctc gtttacgcca ctgcgaacca agagaaaggg   2100
cagaggactc cataccaggc ccttgacagc atggacgacg cctggagttt tagggaatta   2160
aaagcttttg tacgtgagtc aaagacgctt tcaaataaaa aaaaggagta cttgctcact   2220
gaagaagaca tctcaaaatt cgacgtgcgc aaaaaattca ttgagcggaa cttagtcgac   2280
actcggtacg catcaagagt agtgttgaac gccctccagg agcactttag ggcacataag   2340
atcgacacca aggtttcagt tgttaggggt cagtttacat cgcagcttag acgccattgg   2400
ggtatagaaa aaacacgtga tacctaccat caccatgcag ttgacgctct catcattgca   2460
gcatcttctc aacttaattt gtggaaaaag caaaagaaca ctctggtctc atatagcgaa   2520
gatcagctgc ttgatattga aaccggcgag ctgatttctg acgacgaata caaagaatct   2580
gtgtttaagg caccatatca acactttgta gacacgctta atctaaaga gtttgaggat   2640 tcgatccttt tcagttacca agtcgactca aaatttaacc gtaagatctc tgatgcaaca   2700
atttatgcga cgaggcaggc caaggtaggt aaggataagg ctgacgaaac ctacgtgctc   2760
ggaaaaatca agatatttta cactcaagat ggatatgatg cattcatgaa gatatataaa   2820
aaggacaaat ctaaattcct tatgtatcgt catgacccac agacattcga gaaagttatt   2880
gagcctatcc tggagaacta tccgaacaag caaataaatg agaagggcaa agaagttcca   2940
tgtaatccgt tcctaaagta caaggaggaa cacggatata ttagaaaata cagcaaaaag   3000
```

-continued

```
ggcaacggcc cagaaatcaa aagccttaag tactacgata gtaaactagg aaaccacatc    3060
gacattacac caaaagactc taataataag gtcgtactgc aaagcgtttc cccatggcgc    3120
gccgatgtgt attttaataa gacaacaggg aagtacgaaa tcttggggtt aaaatatgcg    3180
gatctgcaat tcgaaaaggg aaccggcaca tacaaaattt ctcaagaaaa gtacaacgac    3240
ataaagaaga aggaaggggt cgattctgat tctgaattca agttcacact ctataagaat    3300
gatcttctgc tcgtcaagga cacagagaca aaggagcagc agttgttcag gttcttgtct    3360
agaactatgc aaaacaaaa gcactacgtt gaactgaagc cttacgataa gcaaaaattc    3420 gagggggggcg aggcgcttat aaaggtccta ggaaatgttg caaactctgg gcagtgtaag    3480
aagggcctgg gcaagagcaa cattagcatc tataaggttc gaacggatgt gcttgggaac    3540
cagcatatca tcaaaaacga gggagataaa ccaaagctgg acttcggatc taagaagaga    3600
agaattaaac aagattag                                                   3618
```

<210> SEQ ID NO 2
<211> LENGTH: 1142
<212> TYPE: PRT
<213> ORGANISM: Streptococcus thermophilus

<400> SEQUENCE: 2

```
Met Gly Ser Lys Lys Arg Arg Ile Lys Gln Asp Met Ser Asp Leu Val
1               5                   10                  15

Leu Gly Leu Asp Ile Gly Ile Gly Ser Val Gly Val Gly Ile Leu Asn
                20                  25                  30

Lys Val Thr Gly Glu Ile Ile His Lys Asn Ser Arg Ile Phe Pro Ala
            35                  40                  45

Ala Gln Ala Glu Asn Asn Leu Val Arg Arg Thr Asn Arg Gln Gly Arg
        50                  55                  60

Arg Leu Ala Arg Arg Lys Lys His Arg Val Arg Leu Asn Arg Leu
65                  70                  75                  80

Phe Glu Glu Ser Gly Leu Ile Thr Asp Phe Thr Lys Ile Ser Ile Asn
                85                  90                  95

Leu Asn Pro Tyr Gln Leu Arg Val Lys Gly Leu Thr Asp Glu Leu Ser
            100                 105                 110

Asn Glu Glu Leu Phe Ile Ala Leu Lys Asn Met Val Lys His Arg Gly
        115                 120                 125

Ile Ser Tyr Leu Asp Asp Ala Ser Asp Gly Asn Ser Ser Val Gly
    130                 135                 140

Asp Tyr Ala Gln Ile Val Lys Glu Asn Ser Lys Gln Leu Glu Thr Lys
145                 150                 155                 160

Thr Pro Gly Gln Ile Gln Leu Glu Arg Tyr Gln Thr Tyr Gly Gln Leu
                165                 170                 175

Arg Gly Asp Phe Thr Val Glu Lys Asp Gly Lys Lys His Arg Leu Ile
            180                 185                 190

Asn Val Phe Pro Thr Ser Ala Tyr Arg Ser Glu Ala Leu Arg Ile Leu
        195                 200                 205

Gln Thr Gln Gln Glu Phe Asn Pro Gln Ile Thr Asp Glu Phe Ile Asn
    210                 215                 220

Arg Tyr Leu Glu Ile Leu Thr Gly Lys Arg Lys Tyr Tyr His Gly Pro
225                 230                 235                 240

Gly Asn Glu Lys Ser Arg Thr Asp Tyr Gly Arg Tyr Arg Thr Ser Gly
                245                 250                 255
```

-continued

```
Glu Thr Leu Asp Asn Ile Phe Gly Ile Leu Ile Gly Lys Cys Thr Phe
            260                 265                 270

Tyr Pro Asp Glu Phe Arg Ala Ala Lys Ala Ser Tyr Thr Ala Gln Glu
        275                 280                 285

Phe Asn Leu Leu Asn Asp Leu Asn Asn Leu Thr Val Pro Thr Glu Thr
    290                 295                 300

Lys Lys Leu Ser Lys Glu Gln Lys Asn Gln Ile Ile Asn Tyr Val Lys
305                 310                 315                 320

Asn Glu Lys Ala Met Gly Pro Ala Lys Leu Phe Lys Tyr Ile Ala Lys
                325                 330                 335

Leu Leu Ser Cys Asp Val Ala Asp Ile Lys Gly Tyr Arg Ile Asp Lys
            340                 345                 350

Ser Gly Lys Ala Glu Ile His Thr Phe Glu Ala Tyr Arg Lys Met Lys
        355                 360                 365

Thr Leu Glu Thr Leu Asp Ile Glu Gln Met Asp Arg Glu Thr Leu Asp
    370                 375                 380

Lys Leu Ala Tyr Val Leu Thr Leu Asn Thr Glu Arg Glu Gly Ile Gln
385                 390                 395                 400

Glu Ala Leu Glu His Glu Phe Ala Asp Gly Ser Phe Ser Gln Lys Gln
                405                 410                 415

Val Asp Glu Leu Val Gln Phe Arg Lys Ala Asn Ser Ser Ile Phe Gly
            420                 425                 430

Lys Gly Trp His Asn Phe Ser Val Lys Leu Met Met Glu Leu Ile Pro
        435                 440                 445

Glu Leu Tyr Glu Thr Ser Glu Glu Gln Met Thr Ile Leu Thr Arg Leu
    450                 455                 460

Gly Lys Gln Lys Thr Thr Ser Ser Asn Lys Thr Lys Tyr Ile Asp
465                 470                 475                 480

Glu Lys Leu Leu Thr Glu Ile Tyr Asn Pro Val Val Ala Lys Ser
                485                 490                 495

Val Arg Gln Ala Ile Lys Ile Val Asn Ala Ala Ile Lys Glu Tyr Gly
            500                 505                 510

Asp Phe Asp Asn Ile Val Ile Glu Met Ala Arg Glu Thr Asn Glu Asp
        515                 520                 525

Asp Glu Lys Lys Ala Ile Gln Lys Ile Gln Lys Ala Asn Lys Asp Glu
    530                 535                 540

Lys Asp Ala Ala Met Leu Lys Ala Ala Asn Gln Tyr Asn Gly Lys Ala
545                 550                 555                 560

Glu Leu Pro His Ser Val Phe His Gly His Lys Gln Leu Ala Thr Lys
                565                 570                 575

Ile Arg Leu Trp His Gln Gln Gly Glu Arg Cys Leu Tyr Thr Gly Lys
            580                 585                 590

Thr Ile Ser Ile His Asp Leu Ile Asn Asn Ser Asn Gln Phe Glu Val
    595                 600                 605

Asp His Ile Leu Pro Leu Ser Ile Thr Phe Asp Asp Ser Leu Ala Asn
610                 615                 620

Lys Val Leu Val Tyr Ala Thr Ala Asn Gln Glu Lys Gly Gln Arg Thr
625                 630                 635                 640

Pro Tyr Gln Ala Leu Asp Ser Met Asp Asp Ala Trp Ser Phe Arg Glu
                645                 650                 655

Leu Lys Ala Phe Val Arg Glu Ser Lys Thr Leu Ser Asn Lys Lys Lys
            660                 665                 670

Glu Tyr Leu Leu Thr Glu Glu Asp Ile Ser Lys Phe Asp Val Arg Lys
```

-continued

```
                675                 680                 685
Lys Phe Ile Glu Arg Asn Leu Val Asp Thr Arg Tyr Ala Ser Arg Val
690                 695                 700

Val Leu Asn Ala Leu Gln Glu His Phe Arg Ala His Lys Ile Asp Thr
705                 710                 715                 720

Lys Val Ser Val Val Arg Gly Gln Phe Thr Ser Gln Leu Arg Arg His
                725                 730                 735

Trp Gly Ile Glu Lys Thr Arg Asp Thr Tyr His His His Ala Val Asp
                740                 745                 750

Ala Leu Ile Ile Ala Ala Ser Ser Gln Leu Asn Leu Trp Lys Lys Gln
                755                 760                 765

Lys Asn Thr Leu Val Ser Tyr Ser Glu Asp Gln Leu Leu Asp Ile Glu
770                 775                 780

Thr Gly Glu Leu Ile Ser Asp Asp Glu Tyr Lys Glu Ser Val Phe Lys
785                 790                 795                 800

Ala Pro Tyr Gln His Phe Val Asp Thr Leu Lys Ser Lys Glu Phe Glu
                805                 810                 815

Asp Ser Ile Leu Phe Ser Tyr Gln Val Asp Ser Lys Phe Asn Arg Lys
                820                 825                 830

Ile Ser Asp Ala Thr Ile Tyr Ala Thr Arg Gln Ala Lys Val Gly Lys
                835                 840                 845

Asp Lys Ala Asp Glu Thr Tyr Val Leu Gly Lys Ile Lys Asp Ile Tyr
850                 855                 860

Thr Gln Asp Gly Tyr Asp Ala Phe Met Lys Ile Tyr Lys Lys Asp Lys
865                 870                 875                 880

Ser Lys Phe Leu Met Tyr Arg His Asp Pro Gln Thr Phe Glu Lys Val
                885                 890                 895

Ile Glu Pro Ile Leu Glu Asn Tyr Pro Asn Lys Gln Ile Asn Glu Lys
                900                 905                 910

Gly Lys Glu Val Pro Cys Asn Pro Phe Leu Lys Tyr Lys Glu Glu His
                915                 920                 925

Gly Tyr Ile Arg Lys Tyr Ser Lys Lys Gly Asn Gly Pro Glu Ile Lys
                930                 935                 940

Ser Leu Lys Tyr Tyr Asp Ser Lys Leu Gly Asn His Ile Asp Ile Thr
945                 950                 955                 960

Pro Lys Asp Ser Asn Asn Lys Val Val Leu Gln Ser Val Ser Pro Trp
                965                 970                 975

Arg Ala Asp Val Tyr Phe Asn Lys Thr Thr Gly Lys Tyr Glu Ile Leu
                980                 985                 990

Gly Leu Lys Tyr Ala Asp Leu Gln Phe Glu Lys Gly Thr Gly Thr Tyr
                995                 1000                1005

Lys Ile Ser Gln Glu Lys Tyr Asn Asp Ile Lys Lys Lys Glu Gly
        1010                1015                1020

Val Asp Ser Asp Ser Glu Phe Lys Phe Thr Leu Tyr Lys Asn Asp
        1025                1030                1035

Leu Leu Leu Val Lys Asp Thr Glu Thr Lys Glu Gln Gln Leu Phe
        1040                1045                1050

Arg Phe Leu Ser Arg Thr Met Pro Lys Gln Lys His Tyr Val Glu
        1055                1060                1065

Leu Lys Pro Tyr Asp Lys Gln Lys Phe Glu Gly Gly Glu Ala Leu
        1070                1075                1080

Ile Lys Val Leu Gly Asn Val Ala Asn Ser Gly Gln Cys Lys Lys
        1085                1090                1095
```

```
Gly Leu Gly Lys Ser Asn Ile Ser Ile Tyr Lys Val Arg Thr Asp
    1100            1105                1110

Val Leu Gly Asn Gln His Ile Ile Lys Asn Glu Gly Asp Lys Pro
    1115            1120                1125

Lys Leu Asp Phe Gly Ser Lys Lys Arg Arg Ile Lys Gln Asp
    1130            1135                1140

<210> SEQ ID NO 3
<211> LENGTH: 1239
<212> TYPE: DNA
<213> ORGANISM: Dahlia mosaic virus

<400> SEQUENCE: 3
atcaacggag aaacaaagat aaaaatcaat tactcacatg aaagagtatt gatcacgagt         60
cactatggag cgacaatctc cagacaggat gtcagcatct tatcttcctt tgaagaaagc        120
atcatcaata acgatgtaat ggtggggaca tccactaagt tattgctctg caaacagctc        180
aaaaagctac tggccgacaa tcataattgc tcggcatgtg caggtggggc ctccactagc        240
aataatacaa gctttacagc ttgcagtgac tcatcctcca ataatggaga aaaagacgtc        300
agcagtgacg aacaagggtc gaaagacttg cctatataag ggcattctcc cctcagttga        360
agatcatcga agttggagc aataaactct ctcttcaaca aatctatctt ttatctttta         420
tcggcgcgcc gggccaccgt cttcggtacg cgctcactcc gccctctgcc tttgttactg        480
ccacgtttct ctgaatgctc tcttgtgtgg tgattgctga gagtggttta gctggatcta        540
gaattacact ctgaaatcgt gttctgcctg tgctgattac ttgccgtcct ttgtagcagc        600
aaaatatagg gacatggtag tacgaaacga agatagaacc tacacagcaa tacgagaaat        660
gtgtaatttg gtgcttagcg gtatttattt aagcacatgt tggtgttata gggcacttgg        720
attcagaagt ttgctgttaa tttaggcaca gcttcatac tacatgggtc aatagtatag         780
ggattcatat tataggcgat actataataa tttgttcgtc tgcagagctt attatttgcc        840
aaaattagat attcctattc tgtttttgtt tgtgtgctgt taaattgtta acgcctgaag        900
gaataaatat aaatgacgaa attttgatgt ttatctctgc tcctttattg tgaccataag        960
tcaagatcag atgcacttgt tttaaatatt gttgtctgaa gaaataagta ctgacagtat       1020
tttgatgcat tgatctgctt gtttgttgta acaaaattta aaaataaaga gtttcctttt       1080
tgttgctctc cttacctcct gatggtatct agtatctacc aactgacact atattgcttc       1140
tctttacata cgtatcttgc tcgatgcctt ctccctagtg ttgaccagtg ttactcacat       1200
agtctttgct catttcattg taatgcagat accaagcgg                             1239

<210> SEQ ID NO 4
<211> LENGTH: 200
<212> TYPE: DNA
<213> ORGANISM: Zea mays

<400> SEQUENCE: 4
cggcgtatgt gccaaaaact tcgtcacaga gagggccata agaaacatgg cccacggccc         60
aatacgaagc accgcgacga agcccaaaca gcagtccgta ggtggagcaa agcgctgggt        120
aatacgcaaa cgttttgtcc caccttgact aatcacaaga gtggagcgta ccttataaac        180
cgagccgcaa gcaccgaatt                                                    200

<210> SEQ ID NO 5
<211> LENGTH: 133
```

```
<212> TYPE: DNA
<213> ORGANISM: Artificial Sequence
<220> FEATURE:
<223> OTHER INFORMATION: Synthetic Sequence

<400> SEQUENCE: 5
gttattgtac tctcaagatt tattttcca aagggttac ttaaatcttg cagaagctac    60
aaagataagg cttcatgccg aaatcaacac cctgtcattt tatggcaggg tgttttcgtt  120 atttaattt ttt                                                      133

<210> SEQ ID NO 6
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 6
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt ggtgcgcggc ctccaggtcc ccgttattgt actctcaaga   240 tttattttc caaagggtt acttaaatct tgcagaagct acaaagataa ggcttcatgc     300
cgaaatcaac accctgtcat ttatggcag gtgttttcg ttatttaatt ttttt          355

<210> SEQ ID NO 7
<211> LENGTH: 20
<212> TYPE: DNA
<213> ORGANISM: Zea mays

<400> SEQUENCE: 7
tacagtccgc cgatcatgac                                               20

<210> SEQ ID NO 8
<211> LENGTH: 20
<212> TYPE: DNA
<213> ORGANISM: Zea mays

<400> SEQUENCE: 8
tgggcggctg ctcggtctcc                                               20

<210> SEQ ID NO 9
<211> LENGTH: 20
<212> TYPE: DNA
<213> ORGANISM: Zea mays

<400> SEQUENCE: 9
tccgccggcg ccaatgacag                                               20

<210> SEQ ID NO 10
<211> LENGTH: 20
<212> TYPE: DNA
<213> ORGANISM: Zea mays

<400> SEQUENCE: 10
gaggcccgca cgtcggtgtc                                               20

<210> SEQ ID NO 11
<211> LENGTH: 20
<212> TYPE: DNA
```

<213> ORGANISM: Zea mays

<400> SEQUENCE: 11
ttcccggcgg gcacgctcag                                                    20

<210> SEQ ID NO 12
<211> LENGTH: 20
<212> TYPE: DNA
<213> ORGANISM: Zea mays

<400> SEQUENCE: 12
atcgcctggt tcgacgcgga                                                    20

<210> SEQ ID NO 13
<211> LENGTH: 20
<212> TYPE: DNA
<213> ORGANISM: Zea mays

<400> SEQUENCE: 13
gaccgcatct ccgtcatcgt                                                    20

<210> SEQ ID NO 14
<211> LENGTH: 20
<212> TYPE: DNA
<213> ORGANISM: Zea mays

<400> SEQUENCE: 14
gtcgtgggcg ccaccgtgct                                                    20

<210> SEQ ID NO 15
<211> LENGTH: 20
<212> TYPE: DNA
<213> ORGANISM: Zea mays

<400> SEQUENCE: 15
tgcgcggcct ccaggtcccc                                                    20

<210> SEQ ID NO 16
<211> LENGTH: 20
<212> TYPE: DNA
<213> ORGANISM: Zea mays

<400> SEQUENCE: 16
atgtccggcc gcgacgggta                                                    20

<210> SEQ ID NO 17
<211> LENGTH: 20
<212> TYPE: DNA
<213> ORGANISM: Zea mays

<400> SEQUENCE: 17
ctgttcgcga cgagcatcag                                                    20

<210> SEQ ID NO 18
<211> LENGTH: 90
<212> TYPE: DNA
<213> ORGANISM: Artificial Sequence
<220> FEATURE:
<223> OTHER INFORMATION: Synthetic Sequence

<400> SEQUENCE: 18
ttaagggata acagggtaat atagcgtaac tataacggtc ctaaggtagc gaattacgat        60
acaaggctac ctagcttcgc agttacgcta                                         90

<210> SEQ ID NO 19
<211> LENGTH: 90
<212> TYPE: DNA
<213> ORGANISM: Artificial Sequence
<220> FEATURE:
<223> OTHER INFORMATION: Synthetic Sequence

<400> SEQUENCE: 19
tagcgtaact gcgaagctag gtagccttgt atcgtaattc gctaccttag gaccgttata     60
gttacgctat attaccctgt tatcccttaa     90

<210> SEQ ID NO 20
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 20
gcagggcaaa uccugcugga guuucagagc uaugcuggaa acagcauagc aaguugaaau     60
aaggcuaguc cguuaucaac uugaaaaagu ggcaccgagu cggugcuuuu uuuu     114

<210> SEQ ID NO 21
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 21
ggagugggcg uuggccaccc guuucagagc uaugcuggaa acagcauagc aaguugaaau     60
aaggcuaguc cguuaucaac uugaaaaagu ggcaccgagu cggugcuuuu uuuu     114

<210> SEQ ID NO 22
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 22
gcucgcgcuu cauguaccgc guuucagagc uaugcuggaa acagcauagc aaguugaaau     60
aaggcuaguc cguuaucaac uugaaaaagu ggcaccgagu cggugcuuuu uuuu     114

<210> SEQ ID NO 23
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 23
gucucgcgcu ucauguaccg guuucagagc uaugcuggaa acagcauagc aaguugaaau     60
aaggcuaguc cguuaucaac uugaaaaagu ggcaccgagu cggugcuuuu uuuu     114

<210> SEQ ID NO 24
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 24
gauguucaug aagggcuucu guuucagagc uaugcuggaa acagcauagc aaguugaaau    60
aaggcuaguc cguuaucaac uugaaaaagu ggcaccgagu cggugcuuuu uuuu    114

<210> SEQ ID NO 25
<211> LENGTH: 114
<212> TYPE: RNA
<213> ORGANISM: Artificial Sequence
<220> FEATURE:
<223> OTHER INFORMATION: Synthetic Sequence

<400> SEQUENCE: 25
guucaugaag ggcuucucgg guuucagagc uaugcuggaa acagcauagc aaguugaaau    60
aaggcuaguc cguuaucaac uugaaaaagu ggcaccgagu cggugcuuuu uuuu    114

<210> SEQ ID NO 26
<211> LENGTH: 115
<212> TYPE: RNA
<213> ORGANISM: Artificial Sequence
<220> FEATURE:
<223> OTHER INFORMATION: Synthetic Sequence

<400> SEQUENCE: 26
gaccuggagg ccgcgcacgc cguuucagag cuaugcugga acagcauag caaguugaaa    60 uaaggcuagu ccguuaucaa cuugaaaaag uggcaccgag ucggugcuuu uuuuu    115

<210> SEQ ID NO 27
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 27
cggcgtatgt gccaaaaact tcgtcacaga gagggccata agaaacatgg cccacggccc    60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt gcagggcaaa tcctgctgga gtttcagagc tatgctggaa    240
acagcatagc aagttgaaat aaggctagtc cgttatcaac ttgaaaaagt ggcaccgagt    300
cggtgctttt tttt    314

<210> SEQ ID NO 28
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 28
cggcgtatgt gccaaaaact tcgtcacaga gagggccata agaaacatgg cccacggccc    60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt ggagtgggcg ttggccaccc gtttcagagc tatgctggaa    240
acagcatagc aagttgaaat aaggctagtc cgttatcaac ttgaaaaagt ggcaccgagt    300
cggtgctttt tttt    314

```
<210> SEQ ID NO 29
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 29
cggcgtatgt gccaaaaact tcgtcacaga gagggccata agaaacatgg cccacggccc      60
aatacgaagc accgcgacga agcccaaaca gcagtccgta ggtggagcaa agcgctgggt     120
aatacgcaaa cgttttgtcc caccttgact aatcacaaga gtggagcgta ccttataaac     180
cgagccgcaa gcaccgaatt gctcgcgctt catgtaccgc gtttcagagc tatgctggaa     240
acagcatagc aagttgaaat aaggctagtc cgttatcaac ttgaaaaagt ggcaccgagt     300
cggtgctttt tttt                                                        314

<210> SEQ ID NO 30
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 30
cggcgtatgt gccaaaaact tcgtcacaga gagggccata agaaacatgg cccacggccc      60
aatacgaagc accgcgacga agcccaaaca gcagtccgta ggtggagcaa agcgctgggt     120
aatacgcaaa cgttttgtcc caccttgact aatcacaaga gtggagcgta ccttataaac     180
cgagccgcaa gcaccgaatt gtctcgcgct tcatgtaccg gtttcagagc tatgctggaa     240
acagcatagc aagttgaaat aaggctagtc cgttatcaac ttgaaaaagt ggcaccgagt     300
cggtgctttt tttt                                                        314

<210> SEQ ID NO 31
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 31
cggcgtatgt gccaaaaact tcgtcacaga gagggccata agaaacatgg cccacggccc      60
aatacgaagc accgcgacga agcccaaaca gcagtccgta ggtggagcaa agcgctgggt     120
aatacgcaaa cgttttgtcc caccttgact aatcacaaga gtggagcgta ccttataaac     180
cgagccgcaa gcaccgaatt gatgttcatg aagggcttct gtttcagagc tatgctggaa     240
acagcatagc aagttgaaat aaggctagtc cgttatcaac ttgaaaaagt ggcaccgagt     300
cggtgctttt tttt                                                        314

<210> SEQ ID NO 32
<211> LENGTH: 314
<212> TYPE: DNA
<213> ORGANISM: Artificial Sequence
<220> FEATURE:
<223> OTHER INFORMATION: Synthetic Sequence

<400> SEQUENCE: 32
cggcgtatgt gccaaaaact tcgtcacaga gagggccata agaaacatgg cccacggccc      60
aatacgaagc accgcgacga agcccaaaca gcagtccgta ggtggagcaa agcgctgggt     120
```

```
aatacgcaaa cgttttgtcc caccttgact aatcacaaga gtggagcgta ccttataaac    180
cgagccgcaa gcaccgaatt gttcatgaag ggcttctcgg gtttcagagc tatgctggaa    240
acagcatagc aagttgaaat aaggctagtc cgttatcaac ttgaaaaagt ggcaccgagt    300
cggtgctttt tttt                                                      314

<210> SEQ ID NO 33
<211> LENGTH: 315
<212> TYPE: DNA
<213> ORGANISM: Artificial Sequence
<220> FEATURE:
<223> OTHER INFORMATION: Synthetic Sequence

<400> SEQUENCE: 33
cggcgtatgt gccaaaaact tcgtcacaga gagggccata agaaacatgg cccacggccc     60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt gacctggagg ccgcgcacgc cgtttcagag ctatgctgga    240
aacagcatag caagttgaaa taaggctagt ccgttatcaa cttgaaaaag tggcaccgag    300
tcggtgcttt ttttt                                                     315

<210> SEQ ID NO 34
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 34
cggcgtatgt gccaaaaact tcgtcacaga gagggccata agaaacatgg cccacggccc     60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt ggtacagtcc gccgatcatg acgttattgt actctcaaga    240 tttattttc caaagggtt acttaaatct tgcagaagct acaaagataa ggcttcatgc    300
cgaaatcaac accctgtcat tttatggcag ggtgttttcg ttatttaatt ttttt         355

<210> SEQ ID NO 35
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 35
cggcgtatgt gccaaaaact tcgtcacaga gagggccata agaaacatgg cccacggccc     60
aatacgaagc accgcgacga agcccaaaca gcagtccgta ggtggagcaa agcgctgggt    120
aatacgcaaa cgttttgtcc caccttgact aatcacaaga gtggagcgta ccttataaac    180
cgagccgcaa gcaccgaatt ggtgggcggc tgctcggtct ccgttattgt actctcaaga    240 tttattttc caaagggtt acttaaatct tgcagaagct acaaagataa ggcttcatgc    300
cgaaatcaac accctgtcat tttatggcag ggtgttttcg ttatttaatt ttttt         355

<210> SEQ ID NO 36
<211> LENGTH: 355
<212> TYPE: DNA
<213> ORGANISM: Artificial Sequence
```

```
<220> FEATURE:
<223> OTHER INFORMATION: Synthetic Sequence

<400> SEQUENCE: 36
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt ggtccgccgg cgccaatgac aggttattgt actctcaaga   240 tttattttc  caaaagggtt acttaaatct tgcagaagct acaaagataa ggcttcatgc   300
cgaaatcaac accctgtcat tttatggcag ggtgttttcg ttatttaatt ttttt        355

<210> SEQ ID NO 37
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 37
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt gggaggcccg cacgtcggtg tcgttattgt actctcaaga   240 tttattttc  caaaagggtt acttaaatct tgcagaagct acaaagataa ggcttcatgc   300
cgaaatcaac accctgtcat tttatggcag ggtgttttcg ttatttaatt ttttt        355

<210> SEQ ID NO 38
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 38
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt ggttcccggc gggcacgctc aggttattgt actctcaaga   240 tttattttc  caaaagggtt acttaaatct tgcagaagct acaaagataa ggcttcatgc   300
cgaaatcaac accctgtcat tttatggcag ggtgttttcg ttatttaatt ttttt        355

<210> SEQ ID NO 39
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 39
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt ggatcgcctg gttcgacgcg gagttattgt actctcaaga   240
``` tttattttc caaaagggtt acttaaatct tgcagaagct acaaagataa ggcttcatgc    300
cgaaatcaac accctgtcat tttatggcag ggtgttttcg ttatttaatt ttttt        355

<210> SEQ ID NO 40
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 40
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt gggaccgcat ctccgtcatc gtgttattgt actctcaaga   240 tttattttc caaaagggtt acttaaatct tgcagaagct acaaagataa ggcttcatgc    300
cgaaatcaac accctgtcat tttatggcag ggtgttttcg ttatttaatt ttttt        355

<210> SEQ ID NO 41
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 41
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt gggtcgtggg cgccaccgtg ctgttattgt actctcaaga   240 tttattttc caaaagggtt acttaaatct tgcagaagct acaaagataa ggcttcatgc    300
cgaaatcaac accctgtcat tttatggcag ggtgttttcg ttatttaatt ttttt        355

<210> SEQ ID NO 42
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 42
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt ggatgtccgg ccgcgacggg tagttattgt actctcaaga   240 tttattttc caaaagggtt acttaaatct tgcagaagct acaaagataa ggcttcatgc    300
cgaaatcaac accctgtcat tttatggcag ggtgttttcg ttatttaatt ttttt        355

<210> SEQ ID NO 43
<211> LENGTH: 355
<212> TYPE: DNA
<213> ORGANISM: Artificial Sequence
<220> FEATURE:
<223> OTHER INFORMATION: Synthetic Sequence

<400> SEQUENCE: 43

```
cggcgtatgt gccaaaaact tcgtcacaga gagggccata agaaacatgg cccacggccc       60
aatacgaagc accgcgacga agcccaaaca gcagtccgta ggtggagcaa agcgctgggt      120
aatacgcaaa cgttttgtcc caccttgact aatcacaaga gtggagcgta ccttataaac      180
cgagccgcaa gcaccgaatt ggctgttcgc gacgagcatc aggttattgt actctcaaga      240
tttatttttc caaaagggtt acttaaatct tgcagaagct acaaagataa ggcttcatgc      300
cgaaatcaac accctgtcat tttatggcag ggtgttttcg ttatttaatt ttttt          355
```